United States Patent
Kimura et al.

(10) Patent No.: US 10,449,016 B2
(45) Date of Patent: Oct. 22, 2019

(54) ARCH ADJUSTMENT APPLIANCE

(71) Applicant: Align Technology, Inc., San Jose, CA (US)

(72) Inventors: Ryan Kimura, San Jose, CA (US); John Morton, San Jose, CA (US); Richard Shaw, Morgan Hill, CA (US); Chunhua Li, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 14/850,305

(22) Filed: Sep. 10, 2015

(65) Prior Publication Data

US 2016/0081769 A1    Mar. 24, 2016

Related U.S. Application Data

(60) Provisional application No. 62/052,893, filed on Sep. 19, 2014.

(51) Int. Cl.
*A61C 3/00* (2006.01)
*A61C 7/10* (2006.01)
*A61C 7/08* (2006.01)
*A61C 7/00* (2006.01)

(52) U.S. Cl.
CPC ............. *A61C 7/10* (2013.01); *A61C 7/002* (2013.01); *A61C 7/08* (2013.01)

(58) Field of Classification Search
CPC ............. A61C 7/10; A61C 7/002; A61C 7/08
See application file for complete search history.

(56) References Cited

U.S. PATENT DOCUMENTS

| | | |
|---|---|---|
| 2,171,695 A | 9/1939 | Harper |
| 2,467,432 A | 4/1949 | Kesling |
| 2,531,222 A | 11/1950 | Kesling |
| 3,092,907 A | 6/1963 | Traiger |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |

(Continued)

FOREIGN PATENT DOCUMENTS

| | | |
|---|---|---|
| AU | 517102 B | 11/1977 |
| AU | 3031677 A | 11/1977 |

(Continued)

OTHER PUBLICATIONS

US 8,553,966 B1, 10/2013, Alpern et al. (withdrawn)

(Continued)

*Primary Examiner* — Nicholas D Lucchesi
(74) *Attorney, Agent, or Firm* — Shay Glenn LLP

(57) ABSTRACT

The present disclosure provides method, systems, and devices for adjusting an arch of teeth. An appliance includes a removable shell formed of a first material having a number of cavities formed therein, wherein the number of cavities are shaped to receive teeth of a patient, and an arch element extending from the removable shell in a lingual direction and across at least a portion of the arch width of the removable shell, wherein the arch element is designed to expand an arch of the teeth of the patient, wherein the arch element has a width specific to a stage of a treatment plan.

14 Claims, 16 Drawing Sheets

(56) References Cited

U.S. PATENT DOCUMENTS

| | | |
|---|---|---|
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,134,208 A | 1/1979 | Pearlman |
| 4,195,046 A | 3/1980 | Kesling |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,629,424 A | 12/1986 | Lauks et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,204,670 A | 4/1993 | Stinton |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,499,633 A | 3/1996 | Fenton |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,174 A | 9/1998 | Andersson |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,904,479 A | 5/1999 | Staples |
| 5,934,288 A | 8/1999 | Avila et al. |

(56) References Cited

U.S. PATENT DOCUMENTS

| | | |
|---|---|---|
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,980,246 A | 11/1999 | Ramsay et al. |
| 5,989,023 A | 11/1999 | Summer et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,099,303 A | 8/2000 | Gibbs et al. |
| 6,099,314 A | 8/2000 | Kopelman et al. |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,217,334 B1 | 4/2001 | Hultgren |
| 6,230,142 B1 | 5/2001 | Benigno et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,299,438 B1 * | 10/2001 | Sahagian ............... A61C 7/00 433/2 |
| 6,309,215 B1 | 10/2001 | Phan et al. |
| 6,315,553 B1 | 11/2001 | Sachdeva et al. |
| 6,238,745 B1 | 12/2001 | Ascherman |
| 6,328,745 B1 | 12/2001 | Ascherman |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,402,510 B1 | 6/2002 | Williams |
| 6,402,707 B1 | 6/2002 | Ernst |
| 6,405,729 B1 | 6/2002 | Thornton |
| 6,413,086 B1 | 7/2002 | Womack |
| 6,436,058 B1 | 8/2002 | Krahner et al. |
| 6,450,167 B1 | 9/2002 | David et al. |
| 6,450,807 B1 | 9/2002 | Chishti et al. |
| 6,482,298 B1 | 11/2002 | Bhatnagar |
| 6,499,995 B1 | 12/2002 | Schwartz |
| 6,515,593 B1 | 2/2003 | Stark et al. |
| 6,516,805 B1 | 2/2003 | Thornton |
| 6,520,772 B2 | 2/2003 | Williams |
| 6,524,101 B1 | 2/2003 | Phan et al. |
| 6,540,707 B1 | 4/2003 | Stark et al. |
| 6,572,372 B1 * | 6/2003 | Phan ............... A61C 7/00 433/18 |
| 6,573,998 B2 | 6/2003 | Cohen Sabban |
| 6,594,539 B1 | 7/2003 | Geng |
| 6,597,934 B1 | 7/2003 | de Jong et al. |
| 6,602,070 B2 | 8/2003 | Miller et al. |
| 6,604,527 B1 | 8/2003 | Palmisano |
| 6,611,783 B2 | 8/2003 | Kelly et al. |
| 6,613,001 B1 | 9/2003 | Dworkin |
| 6,616,579 B1 | 9/2003 | Reinbold et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,640,128 B2 | 10/2003 | Vilsmeier et al. |
| 6,697,164 B1 | 2/2004 | Babayoff et al. |
| 6,702,765 B2 | 3/2004 | Robbins et al. |
| 6,702,804 B1 | 3/2004 | Ritter et al. |
| 6,705,863 B2 | 3/2004 | Phan et al. |
| 6,736,638 B1 | 5/2004 | Sachdeva et al. |
| 6,830,450 B2 | 12/2004 | Knopp et al. |
| 6,832,912 B2 | 12/2004 | Mao |
| 6,885,464 B1 | 4/2005 | Pfeiffer et al. |
| 6,890,285 B2 | 5/2005 | Rahman et al. |
| 6,976,841 B1 | 12/2005 | Osterwalder |
| 6,983,752 B2 | 1/2006 | Garabadian |
| 7,036,514 B2 | 5/2006 | Heck |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,138,640 B1 | 11/2006 | Delgado et al. |
| 7,142,312 B2 | 11/2006 | Quadling et al. |
| 7,166,063 B2 | 1/2007 | Rahman et al. |
| 7,184,150 B2 | 2/2007 | Quadling et al. |
| 7,192,273 B2 | 3/2007 | McSurdy |
| 7,220,124 B2 | 5/2007 | Taub et al. |
| 7,229,282 B2 | 6/2007 | Andreiko et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,500,851 B2 * | 3/2009 | Williams ............... A61C 7/10 433/18 |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,724,375 B1 | 5/2010 | Babayoff |
| D618,619 S | 6/2010 | Walter |
| 7,731,508 B2 | 6/2010 | Borst |
| 7,735,217 B2 | 6/2010 | Borst |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,849 B2 | 1/2011 | Sticker et al. |
| 7,878,801 B2 | 2/2011 | Abolfathi et al. |
| 7,907,280 B2 | 3/2011 | Johs et al. |
| 7,929,151 B2 | 4/2011 | Liang et al. |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 8,017,891 B2 | 9/2011 | Nevin |
| 8,026,916 B2 | 9/2011 | Wen |
| 8,027,709 B2 | 9/2011 | Arnone et al. |

(56) References Cited

U.S. PATENT DOCUMENTS

| | | |
|---|---|---|
| 8,029,277 B2 | 10/2011 | Imgrund et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,160,334 B2 | 4/2012 | Thiel et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 * | 10/2012 | Brandt ............... A61C 7/08 433/22 |
| 8,294,657 B2 | 10/2012 | Kim et al. |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,433,083 B2 | 4/2013 | Abolfathi et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,870,566 B2 | 10/2014 | Bergersen |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rösch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,220,580 B2 | 12/2015 | Borovinskih et al. |
| 9,242,118 B2 | 1/2016 | Brawn |
| 9,261,358 B2 | 2/2016 | Atiya et al. |
| 9,336,336 B2 | 5/2016 | Deichmann et al. |
| 9,408,743 B1 | 8/2016 | Wagner |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,584,771 B2 | 2/2017 | Mandelis et al. |
| 9,610,141 B2 * | 4/2017 | Kopelman ............... A61C 7/10 |
| 9,675,427 B2 | 6/2017 | Kopelman |
| 9,675,430 B2 | 6/2017 | Verker et al. |
| 9,693,839 B2 | 7/2017 | Atiya et al. |
| 9,744,006 B2 | 8/2017 | Ross |
| 9,861,451 B1 | 1/2018 | Davis |
| 9,936,186 B2 | 4/2018 | Jesenko et al. |
| 2001/0038705 A1 | 11/2001 | Rubbert et al. |
| 2001/0041320 A1 | 11/2001 | Phan et al. |
| 2002/0010568 A1 | 1/2002 | Rubbert et al. |
| 2002/0015934 A1 | 2/2002 | Rubbert et al. |
| 2003/0009252 A1 | 1/2003 | Pavlovskaia et al. |
| 2003/0035061 A1 | 2/2003 | Iwaki et al. |
| 2003/0059736 A1 | 3/2003 | Lai et al. |
| 2003/0101079 A1 | 5/2003 | McLaughlin |
| 2003/0139834 A1 | 7/2003 | Nikolskiy et al. |
| 2003/0190575 A1 | 10/2003 | Hilliard |
| 2003/0207224 A1 | 11/2003 | Lotte |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0058295 A1 | 3/2004 | Bergersen |
| 2004/0094165 A1 | 5/2004 | Cook |
| 2004/0158194 A1 | 8/2004 | Wolff et al. |
| 2004/0197728 A1 | 10/2004 | Abolfathi et al. |
| 2004/0229185 A1 | 11/2004 | Knopp |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0048433 A1 | 3/2005 | Hilliard |
| 2005/0100333 A1 | 5/2005 | Kerschbaumer et al. |
| 2005/0181333 A1 | 8/2005 | Karazivan et al. |
| 2005/0186524 A1 | 8/2005 | Abolfathi et al. |
| 2005/0244781 A1 | 11/2005 | Abels et al. |
| 2005/0244791 A1 | 11/2005 | Davis et al. |
| 2006/0084024 A1 | 4/2006 | Farrell |
| 2006/0099546 A1 | 5/2006 | Bergersen |
| 2006/0154198 A1 | 7/2006 | Durbin et al. |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2007/0046865 A1 | 3/2007 | Umeda et al. |
| 2007/0053048 A1 | 3/2007 | Kumar et al. |
| 2007/0065768 A1 | 3/2007 | Nadav |
| 2007/0087300 A1 | 4/2007 | Willison et al. |
| 2007/0106138 A1 | 5/2007 | Beiski et al. |
| 2007/0184402 A1 | 8/2007 | Boutoussov et al. |
| 2007/0231765 A1 * | 10/2007 | Phan ................ A61C 7/00 433/6 |
| 2007/0263226 A1 | 11/2007 | Kurtz et al. |
| 2008/0045053 A1 | 2/2008 | Stadler et al. |
| 2008/0057461 A1 | 3/2008 | Cheng et al. |
| 2008/0062429 A1 | 3/2008 | Liang et al. |
| 2008/0090208 A1 | 4/2008 | Rubbert |
| 2008/0115791 A1 | 5/2008 | Heine |
| 2008/0118886 A1 | 5/2008 | Liang et al. |
| 2008/0169122 A1 | 7/2008 | Shiraishi et al. |
| 2008/0176448 A1 | 7/2008 | Muller et al. |
| 2008/0242144 A1 | 10/2008 | Dietz |
| 2008/0306724 A1 | 12/2008 | Kitching et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kaneko et al. |
| 2009/0087050 A1 | 4/2009 | Gandyra |
| 2009/0105523 A1 | 4/2009 | Kassayan et al. |
| 2009/0117507 A1 | 5/2009 | Abolfathi et al. |
| 2009/0170050 A1 | 7/2009 | Marcus |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0317757 A1 | 12/2009 | Lemchen |
| 2010/0015565 A1 | 1/2010 | Gonzalez et al. |
| 2010/0019170 A1 | 1/2010 | Hart et al. |
| 2010/0028825 A1 | 2/2010 | Lemchen |

(56) References Cited

U.S. PATENT DOCUMENTS

| | | |
|---|---|---|
| 2010/0045902 A1 | 2/2010 | Ikeda et al. |
| 2010/0138025 A1 | 6/2010 | Morton et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0196837 A1 | 8/2010 | Farrell |
| 2010/0231577 A1 | 9/2010 | Kim et al. |
| 2010/0312484 A1 | 12/2010 | DuHamel et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0065060 A1 | 3/2011 | Teixeira et al. |
| 2011/0081625 A1 | 4/2011 | Fuh |
| 2011/0102549 A1 | 5/2011 | Takahashi |
| 2011/0102566 A1 | 5/2011 | Zakian et al. |
| 2011/0136090 A1 | 6/2011 | Kazemi |
| 2011/0143673 A1 | 6/2011 | Landesman et al. |
| 2011/0207072 A1 | 8/2011 | Schiemann |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0337412 A1 | 12/2013 | Kwon |
| 2014/0081091 A1 | 3/2014 | Abolfathi et al. |
| 2014/0178829 A1 | 6/2014 | Kim |
| 2014/0186794 A1 | 7/2014 | Deichmann et al. |
| 2014/0272774 A1 | 9/2014 | Dillon et al. |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1 | 11/2014 | Fleer et al. |
| 2014/0363778 A1 | 12/2014 | Parker |
| 2015/0002649 A1 | 1/2015 | Nowak et al. |
| 2015/0079531 A1 | 3/2015 | Heine |
| 2015/0140502 A1 | 5/2015 | Brawn et al. |
| 2015/0164335 A1 | 6/2015 | Van Der Poel et al. |
| 2015/0173856 A1* | 6/2015 | Lowe .................... A61C 7/008 433/24 |
| 2015/0216716 A1 | 8/2015 | Aldecoa |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0325044 A1 | 11/2015 | Lebovitz |
| 2015/0338209 A1 | 11/2015 | Knüttel |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0022185 A1 | 1/2016 | Agarwal et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0106520 A1 | 4/2016 | Borovinskih et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0367188 A1 | 12/2016 | Malik et al. |
| 2017/0007366 A1 | 1/2017 | Kopelman et al. |
| 2017/0007367 A1 | 1/2017 | Li et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0086943 A1 | 3/2017 | Mah |
| 2017/0156821 A1 | 6/2017 | Kopelman et al. |
| 2017/0258555 A1 | 9/2017 | Kopelman |
| 2017/0265970 A1 | 9/2017 | Verker |
| 2017/0325690 A1 | 11/2017 | Salah et al. |
| 2017/0340415 A1 | 11/2017 | Choi et al. |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2019/0046296 A1 | 2/2019 | Kopelman et al. |

FOREIGN PATENT DOCUMENTS

| | | |
|---|---|---|
| CA | 1121955 A1 | 4/1982 |
| CN | 1655732 A | 8/2005 |
| CN | 1655733 A | 8/2005 |
| CN | 103889364 A | 6/2014 |
| CN | 105997274 A | 10/2016 |
| DE | 2749802 A1 | 5/1978 |
| DE | 69327661 T2 | 7/2000 |
| DE | 102005043627 A1 | 3/2007 |
| DE | 202010017014 U1 | 2/2011 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| ES | 2455066 A1 | 4/2014 |
| FR | 2369828 A1 | 6/1978 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 2007260158 A | 10/2007 |
| JP | 2007537824 A | 12/2007 |

(56) References Cited

FOREIGN PATENT DOCUMENTS

| | | | |
|---|---|---|---|
| JP | 2008523370 A | 7/2008 |
| JP | 4184427 B1 | 11/2008 |
| JP | 04184427 B1 | 11/2008 |
| JP | 2009000412 A | 1/2009 |
| JP | 2009000412 A | 1/2009 |
| JP | 2009018173 A | 1/2009 |
| JP | 2011087733 A | 5/2011 |
| JP | 2013007645 A | 1/2013 |
| KR | 10-1266966 B1 | 5/2013 |
| KR | 10-2016-041632 A | 4/2016 |
| KR | 10-2016-0071127 A | 6/2016 |
| TW | 480166 B | 3/2002 |
| WO | WO91/004713 A1 | 4/1991 |
| WO | WO94/010935 A1 | 5/1994 |
| WO | WO98/032394 A1 | 7/1998 |
| WO | WO98/044865 A1 | 10/1998 |
| WO | 0180762 A2 | 11/2001 |
| WO | WO01/85047 A2 | 11/2001 |
| WO | WO02/017776 A2 | 3/2002 |
| WO | WO02/062252 A1 | 8/2002 |
| WO | WO02/095475 A1 | 11/2002 |
| WO | 03003932 A2 | 1/2003 |
| WO | WO03/003932 A2 | 1/2003 |
| WO | WO2006/096558 A2 | 9/2006 |
| WO | WO2006/133548 A1 | 12/2006 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/140021 A2 | 10/2012 |
| WO | WO2014/091865 A1 | 6/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | 2016042393 A1 | 3/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2016/200177 A1 | 12/2016 |
| WO | WO2018/085718 A2 | 5/2018 |

OTHER PUBLICATIONS

International Search Report from related PCT Application No. PCT/IB2016/000729, dated Dec. 15, 2016, 6 pp.
International Search Report and Written Opinion from related PCT Application PCT/IB2015/001653, dated Feb. 4, 2016, 22 pp.
Invitation to Pay Fees and Partial Search Report from related PCT Application PCT/IB2015/001653 dated Dec. 7, 2015, 8 pp.
Begole et al.; A Computer System for the Analysis of Dental Casts; The Angle Orthodontist; 51(3); pp. 252-258; Jul. 1981.
Biggerstaff; Computerized Diagnostic Setups and Simulations; Angle Orthodontist; 40(I); pp. 28-36; Jan. 1970.
Blu et al.; Linear interpolation revitalized; IEEE Transactions on Image Processing; 13(5); pp. 710-719; May 2004.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Gao et al.; 3-D element Generation for Multi-Connected Complex Dental and Mandibular Structure; IEEE Proceedings International Workshop in Medical Imaging and Augmented reality; pp. 267-271; Jun. 12, 2001.
Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Kochanek; Interpolating Splines with Local Tension, Continuity and Bias Control; Computer Graphics; 18(3); pp. 33-41; Jan. 1, 1984.
Kunii et al.; Articulation Simulation for an Intelligent Dental Care System; Displays; 15(3); pp. 181-188; Jul. 1994.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Richmond et al.; The Development of the PAR Index (Peer Assessment Rating): Reliability and Validity.; The European Journal of Orthodontics; 14(2); pp. 125-139; Apr. 1992.
Sturman; Interactive Keyframe Animation of 3-D Articulated Models; Proceedings Graphics Interface '84; vol. 86; pp. 35-40; May-Jun. 1984.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Verstreken et al.; An Image-Guided Planning System for Endosseous Oral Implants; IEEE Transactions on Medical Imaging; 17(5); pp. 842-852; Oct. 1998.
Williams; Dentistry and CAD/CAM: Another French Revolution; J. Dent. Practice Admin.; 4(1); pp. 2-5 Jan./Mar. 1987.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Cramer; U.S. Appl. No. 15/937,569 entitled "Apparatuses and methods assisting in dental therapies," filed Mar. 27, 2018.
Cramer et al.; U.S. Appl. No. 15/942,341 entitled "Orthodontic appliances including at least partially un-erupted teeth and method of forming them," filed Mar. 30, 2018.
Kuo; U.S. Appl. No. 15/829,504 entitled "Dental appliance features for speech enhancement," filed Dec. 1, 2017.
Yamada et al.; Simulation of fan-beam type optical computed-tomography imaging of strongly scattering and weakly absorbing media; Applied Optics; 32(25); pp. 4808-4814; Sep. 1, 1993.
Doruk et al.; The role of the headgear timer in extraoral co-operation; European Journal of Orthodontics; 26; pp. 289-291; Jun. 1, 2004.
Friedrich et al; Measuring system for in vivo recording of force systems in orthodontic treatment-concept and analysis of accuracy; J. Biomech.; 32(1); pp. 81-85; (Abstract Only) Jan. 1999.
Grest, Daniel; Marker-Free Human Motion Capture in Dynamic Cluttered Environments from a Single View-Point, PhD Thesis; 171 pages; Dec. 2007.
Invisalign; You were made to move. There's never been a better time to straighten your teeth with the most advanced clear aligner in the world; Product webpage; 2 pages; retrieved from the internet (www.invisalign.com/) on Dec. 28, 2017.
Kumar et al.; Rapid maxillary expansion: A unique treatment modality in dentistry; J. Clin. Diagn. Res.; 5(4); pp. 906-911; Aug. 2011.

(56) References Cited

OTHER PUBLICATIONS

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 19990.
Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Thera Mon; "Microsensor"; "2 pages"; retrieved from the interent (www.english.thera-mon.com/the-product/transponder/index.html); on Sep. 19, 2016.
Wikipedia; Palatal expansion; 3 pages; retrieved from the internet (https://en.wikipedia.org/wiki/Palatal_expansion) on Mar. 5, 2018.
Wireless Sensor Networks Magazine; Embedded Teeth for Oral Activity Recognition; 2 pages; retrievedon Sep. 19, 2016 from the internet (www.wsnmagazine.com/embedded-teeth/); Jul. 29, 2013.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Carrier et al.; U.S. Appl. No. 15/803,718 entitled "Methods and apparatuses for dental images," filed Nov. 3, 2017.
Atiya et al.; U.S. Appl. No. 15/859,010 entitled "Compact confocal dental scanning apparatus," filed Dec. 29, 2017.
Shanjani et al.; U.S. Appl. No. 15/831,159 entitled "Palatal expanders and methods of expanding a palate," filed Dec. 4, 2017.
Wu et al.; U.S. Appl. No. 15/831,262 entitled "Methods and apparatuses for customizing a rapid palatal expander," filed Dec. 4, 2017.
Grove et al.; U.S. Appl. No. 15/726,243 entitled "Interproximal reduction templates," filed Oct. 5, 2017.

Bernabe et al.; Are the lower incisors the best predictors for the unerupted canine and premolars sums? an analysis of peruvian sample; The Angle Orthodontist; 75(2); pp. 202-207; Mar. 2005.
Collins English Dictionary; Teeth (definition); 9 pages; retrieved from the internet (https:www.collinsdictionary.com/us/dictionary/english/teeth) on May 13, 2019.
Dictionary.com; Plural (definition); 6 pages; retrieved from the internet (https://www.dictionary.com/browse/plural#) on May 13, 2019.
Dictionary.com; Quadrant (definition); 6 pages; retrieved from the internet (https://www.dictionary.com/browse/quadrant?s=t) on May 13, 2019.
Martinelli et al.; Prediction of lower permanent canine and premolars width by correlation Tthe Angle Orthodontist; 75(5); pp. 805-808; Sep. 2005.
Nourallah et al.; New regression equations for predicting the size of unerupted canines and premolars in a contemporary population; The Angle Orthodontist; 72(3); pp. 216-221; Jun. 2002.
Paredes et al.; A new, accurate and fast digital method to predict unerupted tooth size; The Angle Orthodontist; 76(1); pp. 14-19; Jan. 2006.
Video of DICOM to Surgical Guides; [Copy Not Enclosed], Can be viewed at <URL:https://youtu.be/47KtOmCEFQk; Published Apr. 4, 2016.
Dentalwings; Intraoral scanner; 7 pages; retrieved from the internet (https://web.archive.org/web/20160422114335/http://www.dentalwings.com/products/intraoral-scanned); available as of Apr. 4, 2016.
Dentalwings; I series dental impression scanner; 8 pages; retrieved from the internet (https://web.archive.org/web/20160502145908/http://www.dentalwings.com/products/scan-and-design-systems/iseries/) ; available as of May 2, 2016.
3 Shape Trios 3; Insane speed-scanning with 3shape trios 3 intracral canner; (Screenshot); 2 pages; retrieved from the Internet at You Tube (https//www.youtube.com/watch?v=X5CviUZ5DpQ&feature=youtu.be; available as of Sep. 18, 2015.

* cited by examiner

ARCH ADJUSTMENT APPLIANCE

BACKGROUND

The present disclosure is related generally to the field of dental treatment. More particularly, the present disclosure is related to methods, systems, and devices for adjusting an arch of a patient.

Dental treatments may involve, for instance, restorative and/or orthodontic procedures. Restorative procedures may be designed to implant a dental prosthesis (e.g., a crown, bridge inlay, onlay, veneer, etc.) intraorally in a patient. Orthodontic procedures may include repositioning misaligned teeth and/or changing bite configurations for improved cosmetic appearance and/or dental function. Orthodontic repositioning can be accomplished, for example, by applying controlled forces to one or more teeth over a period of time.

As an example, orthodontic repositioning may be provided through a dental process that uses positioning appliances for realigning teeth. Such appliances may utilize a thin shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are lightweight and/or transparent to provide a set of appliances that can be used serially such that as the teeth move, a new appliance can be implemented to further move the teeth toward the desired goal.

In some instances, the width of a dental arch of a patient's upper dentition and/or and a width of a dental arch of a patient's lower dentition can be insufficient (e.g., too narrow) and on rare occasions, the width may be excessive (e.g., Brodie bite). A dental arch that is insufficient can result in malocclusions such as crossbite, crowding of teeth, impacted teeth, and/or the patient's smile may not be aesthetically pleasing in appearance. For instance, a patient's smile may be "narrow", resulting in a sunken appearance in the buccal corridors due to the inability to see the back teeth from the front view.

In certain types of front-to-back bite correction (e.g., Class II and Class III correction), a need for transverse width correction exists, without which the upper and lower arches will not be properly coordinated. For Class II correction, the upper needs to be expanded so that when the lower is advanced, the teeth in the buccal regions (typically the bicuspids and molars) are fitting together correctly in the buccal-lingual dimension. For Class III correction, the reverse is required, and the lower needs to be expanded since it is usually the one that has compensated for the Class III bite by constricting. When both Class II and Class III are corrected to a more ideal Class I bite, the respective compensations need to be undone, and a transverse width dimension of movement is necessary in addition to the anterior-to-posterior movement.

There are several ways in which the arch of a patient can be expanded. For example, palatal expansion expands the upper jaw of the patient by spreading the maxilla. In some situations, the teeth of the upper and/or lower jaw can be moved or angled outward thereby expanding the width of the arch of the patient. This technique can be referred to as dental expansion. Further, expansion of the lower arch in this manner is often referred to as mandibular expansion.

In young patients, the midpalatal suture has not fused the left and right maxillary palates together and therefore, the movement of the plates with respect to each other can be accomplished more easily and with less force than in older patients. When the fusing of the suture is new, it may still be possible to split the suture apart.

For example, currently available orthodontic appliances can include a jackscrew and/or other mechanism that is employed to deliver a horizontal stretching force to the molar teeth to split the upper jaw of the patient along the midpalatal suture. Such a mechanism typically spreads the left and right maxillary plates of the palate apart and then new bone material grows in between to fill the gap. As such, a large horizontal force (e.g., 10 to 50 Newtons (N) with cumulative loads reaching 40 to 150 N across the suture) is applied during a short period, in many cases. The insertion of such a mechanism is typically accomplished by a treatment professional and can cause discomfort and/or pain for a patient.

In some instances, the screw and/or other mechanism can be employed incrementally one or more times a day (e.g., 0.25 mm expansion twice a day—one activation in the morning and once at night). For example, a pinhole can be present in the orthodontic appliance and a patient can insert an activation key into the pinhole to incrementally increase a distance between portions of the orthodontic appliance.

Such orthodontic appliances can be difficult for a patient to use, and often require assistance from another person (e.g., a parent) to turn the key. Not only are such appliances often not aesthetically pleasing, they often times interfere with the patient's speech, temporarily affect their ability to chew and/or swallow, and/or can be painful when activated.

Adding to the challenges of such an appliance is the need to retain the expansion while the bone is filling into the suture, long after the active expansion has taken place. The active expansion process may be completed within 2 or 3 weeks' time, but the retention period can last around 6 months while waiting for the gap between the maxillary halves to fill in with new bony tissue.

DETAILED DESCRIPTION

Figure 1A:
FIG. 1A illustrates an example of an appliance having a structural reinforcement feature provided thereon according to a number of embodiments of the present disclosure.

As discussed above, the present disclosure provides methods, systems, and devices for expanding an arch of a patient. Generally, dental and/or skeletal expansion occurs during an orthodontic treatment which is a process of moving and reorienting teeth for functional and/or aesthetic purposes, although repositioning may be made for other purposes.

In some instances, an arch of a patient's teeth can be insufficient (e.g., narrow), and in rare occasions, too wide. An insufficient arch of a patient's teeth can cause overcrowding of a patient's teeth, impacted teeth, speech difficulty, breathing issues, and/or the smile of a patient can be aesthetically unpleasing. As such, an orthodontic treatment plan can include an arch expansion component and such a process typically occurs in an early stage of the plan in order to provide more room for the teeth to be arranged.

A narrow arch also prevents the anterior-posterior bite relationship from being corrected properly. An arch of teeth, as used herein, can include a curved row of teeth on a particular jaw of a patient. An insufficient arch can include an arch that has a width too narrow to support the row of teeth in a correct alignment, for instance. The arch width of a patient's teeth can be expanded, for instance, using an orthodontic appliance (e.g., a dental appliance).

As discussed above, patients that are children or teenagers may have a maxilla where the midpalatal suture has not yet fused. Usually in the mid to late teens, the palatal suture fuses and the halves of the maxilla join together to become a single maxillary bone.

The maxilla (e.g., the upper jaw) is a bone that is fixed to the skull and forms the palate of the patient. The mandible (e.g., lower jaw) is a bone that is also attached to the skull by numerous muscles which power its movement. The mandible articulates at its posterior upward extremities with the temporal bone to form the jaw joint. The jaw joint is a loosely connected joint that accommodates the variety of movements of the mandible relative to the maxilla during biting and chewing.

In correctly shaped and positioned jaws, the upper teeth occupy an arch that is wider than the arch comprising the lower teeth. In other words, the upper teeth are designed to be buccally positioned relative to the teeth in the lower jaw. Malocclusions, such as crossbite, occur when this normal arrangement is reversed and one or more of the upper teeth are positioned lingual to the teeth in the lower jaw.

A patient with an un-fused maxilla can, for instance, have their palate skeletally expanded. This is in contrast to dental expansion where the teeth are uprighted or moved within the boundaries of the jaw in which they are contained. With skeletal expansion, the underlying bone is moved and the teeth are moved along with the changes to the shape of the bone.

Expanding a palate can, for instance, include splitting the left and right sides of the maxilla so that the teeth on the upper left side move as a single unit relative to the teeth on the right side. Because of this phenomenon, a gap between the top two front teeth can open up during the expansion process if they are not restrained from separating.

As discussed above, expansion of the palate, such as those methods performed prior to an orthodontic treatment involving braces and wires, currently includes having a treatment professional place an orthodontic appliance that may include anchoring bands, support bars, springs, and/or jack screws. The appliance is firmly affixed to the teeth at the anchor points and the springs or jackscrew applies forces on the teeth in order to move the underlying portions of the palate of the patient, thereby causing the arch of the patient's dentition to widen.

To adjust the appliance and increase the amount of expansion, the patient and/or another person must insert a key into the pinhole and turn the key to increase the width of the orthodontic appliances. In some examples, prior approaches can include a removable appliance which contains a jackscrew expander that is activated with a pinhole key.

After expanding the arch of the patient to the desired width (and sometimes overcorrecting in order to anticipate potential relapse toward the narrowness initially present), further orthodontic treatment can be performed to move and re-orient the teeth of the patient. This type of additional orthodontic treatment is typically performed after the expansion phase and a retention period where the jaw position is stabilized for a period of time while the musculature and bone adjust to the new positioning.

Further, palate expansion devices that are used primarily for skeletal expansion are typically temporarily anchored to the molars and/or pre-molars of the patient for the duration of the expansion and cannot be removed except by a dental professional because they are cemented into place. The forces that are applied to the molars and/or premolars are rather high in order to separate the suture during a short time period (e.g., one or more days), and therefore, the treatment can be uncomfortable to the patient due to the high pressure that is generated during the activation period. Once the suture splits, the majority of the pressure is relieved and subsequent activations in close proximity to the initial activation are not as uncomfortable.

In contrast, expanding an arch of a patient (whether skeletally with a fixed appliance or dentally with a removable appliance) according to embodiments of the present disclosure, can include utilizing a set of one or more appliances, such as positioners, retainers, and/or other removable appliances (e.g., clear plastic polymer shells and/or aligners) having a shell to be worn over the teeth of a patient and having an arch element thereon that is designed to expand an arch of teeth of the patient by: moving the teeth of the patient to a wider position within the jaw, by expanding the palate of the patient, or a combination of the two. As indicated, some embodiments discussed herein may also expand the palate to a degree, but the dental expansion is much more gradual (e.g., on the order of 0.5 mm per month as opposed to 0.5 mm per day).

Palatal expansion may be accomplished, for example, in patients where the midpalatal suture has not fused. Additionally, some embodiments may be able to un-fuse the suture, in some patients.

One or more appliance embodiments can include a removable shell formed of a first material having a number of cavities therein, wherein the cavities are shaped to receive teeth of the patient. These appliances are not fixed to the teeth of the patient and therefore can be removed by the patient for periods of time during treatment without aid from other people or intervention by a treatment professional.

Figure 7:
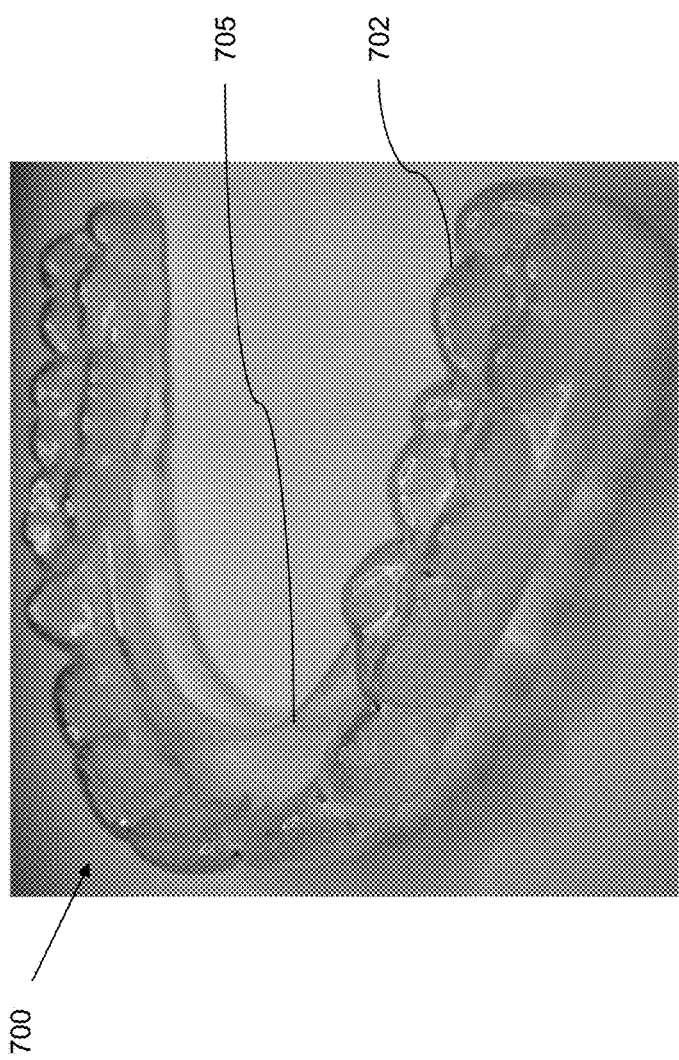
FIG. 7 illustrates an example of an appliance having an anterior tab arch element according to a number of embodiments of the present disclosure.
Figure 9:
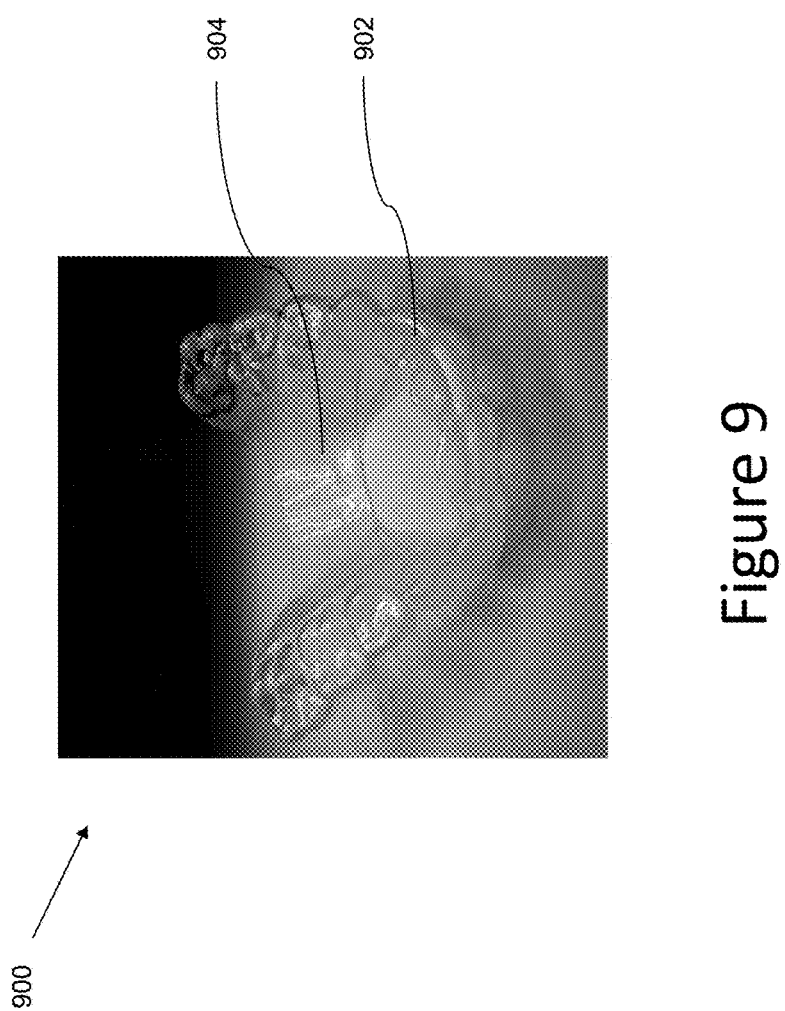
FIG. 9 illustrates an example of an appliance having an arch element connecting the posterior sides of the arch according to a number of embodiments of the present disclosure.
Figure 10:
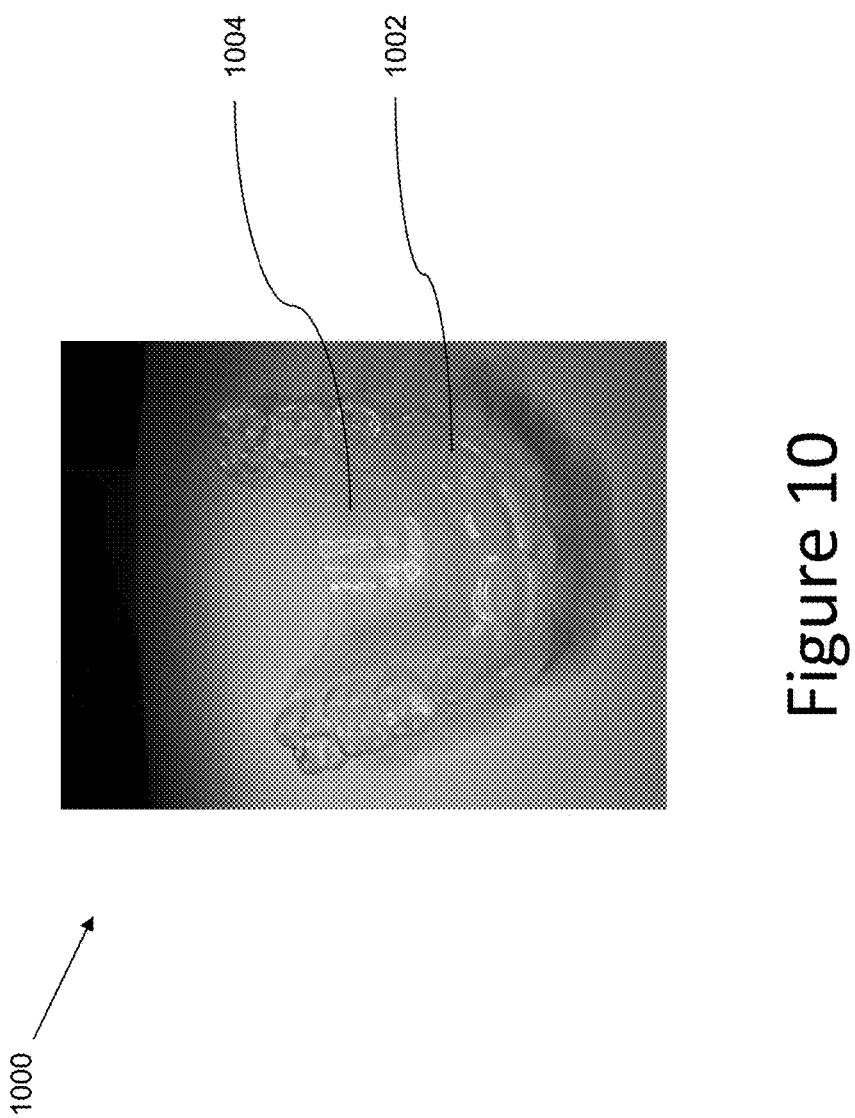
FIG. 10 illustrates an example of an appliance having a full palatal arch element according to a number of embodiments of the present disclosure.
Figure 11:
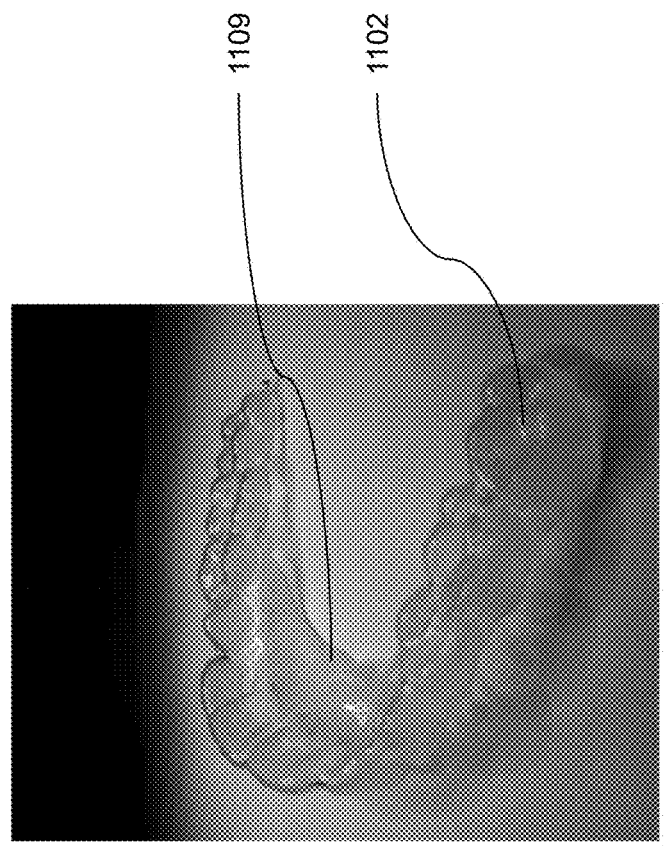
FIG. 11 illustrates an example of an appliance having an extended gingival feature thereon according to a number of embodiments of the present disclosure.

In various embodiments of the present disclosure, an arch element (e.g., a trans-palatal arch element as illustrated in the embodiments of FIGS. 9 and 10 or a mandibular arch element as illustrated in the embodiments of FIGS. 7 and 11) can extend from the removable shell and across at least a portion of the arch width of the removable shell. The arch width can be from molar to molar, from premolar to premolar, from canine to canine, or from any tooth on the left side to any tooth on the right side.

In mandibular arch elements, the arch can extend along the inside of the teeth in the anterior area of the patient's mouth, as shown in FIGS. 7 and 11. In palatal arch elements, the arch element can extend across the palate (trans-palatal) and can extend across at the posterior, anterior, in parts of one or the other, or in both areas of the patient's mouth.

In some embodiments, the arch element can be formed of a first material and from a second material that is a different than the first material in at least one physical property. For example, the first material may be a polyurethane material and the second material also be a polyurethane material with the same chemical formula, but of different hardness or rigidity due to greater crosslinking. Or, the first material can be of one chemical composition (e.g. polyurethane), and the second material of an entirely different chemical composition (e.g. polyvinyl chloride).

In some embodiments, the second material is more resilient than the first material. This can be beneficial in embodiments, for example, where there is an initial need for a more rigid arch element and then a more resilient arch element later in treatment, among other situations where such an embodiment may be utilized.

The arch element can have a width specific to a stage of a treatment plan and can be designed to expand an arch of the teeth of the patient to that specified width, which may be less than the full width in which that arch is to be expanded (i.e., the arch expansion can be incrementally accomplished by expanding the arch a little at a time over the use of several differently designed sequential dental appliances). Or the arch may be over-expanded to compensate for incomplete biological response to the desired outcome, where the actual width of the teeth is less than the width programmed or built into the stage(s) of the treatment plan which can provide a constant transverse expansion force to achieve slow palatal expansion.

For example, rather than providing a strong force, such as 10 to 50 N for a short period of a few days to a few weeks, embodiments of the present disclosure can provide a lesser force, such as 3 to 9 N, for a longer period, such as a month to six months. This force can be used, for example, to move palatal plates, move teeth outward, and/or maintain the teeth and/or jaw in a particular orientation while musculature and bone are adjusting to the orientation and to prevent movement of the teeth or jaw back toward their initial orientation.

In some embodiments, the second material can include, for instance, a more rigid material than the first material designed to provide greater resistance and/or force in a horizontal direction (i.e., transverse direction) against the posterior teeth (e.g., molars and bicuspids) of the arch of the patient. In various embodiments, this second material can be designed to impart force to the molars and/or other teeth on the jaw of the patient in order to either help preserve or change the transverse dimensions of the arch. Additionally, in some embodiments, with the use of appliances on the upper and lower jaws, the force can be imparted to parts of the opposing jaw (e.g., teeth, jaw bone, etc.).

The expansion of an arch of teeth in the patient can be used to treat malocclusions such as crossbites, sagittal problems, crowding, and/or to help prevent or resolve impacted teeth, in various embodiments. The transverse support elements can be designed to not interfere with the shells of the dental appliance. In this manner, a dental appliance in accordance with embodiments of the present disclosure can be used to concurrently expand or constrict an arch of the patient while repositioning a number of teeth of the patient.

For example, in some embodiments, the shell of the dental appliance can be used to provide force on one or more teeth to change their location or orientation. Embodiments of the present disclosure can be utilized to treat Class I, Class II, and Class II malocclusions.

For instance, with Class I malocclusions, teeth of the patient are inserted into cavities in the shell and the shell applies force to one or more teeth to change their location or orientations. With Class II (overbite or overjet) and Class III (underbite) malocclusions, the appliance can include other features, such as cut outs (areas cut out of the appliance shell material to allow access to the tooth surface through the appliance or to form, for example, a hook to attach a resilient member (e.g., an elastic band material) between the upper and lower jaw, to for instance treat a overbite or overjet.

As discussed above, in some embodiments, a plurality of appliances can be worn by a patient successively to achieve gradual expansion (or constriction) of the arch of teeth in the patient. For instance, each of a plurality of dental appliances can include an incrementally wider width to expand the arch of the patient in incremental distances. In some such embodiments, since this arch expansion technique can be accomplished concurrently with other orthodontic treatments, the arch expansion can be accomplished over a series of appliances that will be utilized, for example, over a period of less than six months, thereby making any pain and/or discomfort of the patient more consistent and less arbitrary without prolonging the overall time for orthodontic treatment.

In some embodiments, an appliance can be formed using a thermoforming process. For instance, a first portion of an arch element can be formed of a material using a virtual model of the palate of the patient and a virtual model of a number of teeth of the patient.

The first portion of the arch element can be wider than the arch width of the number of teeth of the first jaw of the patient and can be shaped to substantially follow contours of the palate of the patient. For expansion, this difference in the width will facilitate the movement of the arch outward toward the wider position of the arch element generating a transverse expansion force.

A removable shell can be formed over a set of molded teeth. The removable shell can include a number of cavities formed therein and shaped to receive the number of teeth of patient and a second portion of the arch element. The second portion of the arch element can be formed of the same material as the removable shell and can include the same width as the first portion of the arch element.

The first portion of the arch element and the second portion of the arch element can, for example, be connected to form the dental appliance. The first portion and second portion can be connected, in accordance with various embodiments of the present disclosure, for example, by thermoforming the removable shell over the set of molded teeth with the first portion of the arch element placed within the set of molded teeth (e.g., encapsulated), or via direct fabrication of the arch elements from a virtual model, then by fusing the two materials together (e.g., ultrasonic welding), by adhering the first portion and the second portion using an agent subsequent to forming the first portion and the removable shell, and/or by adding a number of features to the first portion of the arch element (e.g., as discussed further herein).

In this manner, a dental appliance can be formed that has two distinct material properties, but is unitary in nature (e.g., forms a single body that can be used by the patient even though it is formed of two materials). Such embodiments, are discussed with regard to the embodiments illustrated in the figures and discussed below.

In the detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1A, and a similar element may be referenced as 304 in FIG. 3. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

FIG. 1A illustrates an example of an appliance according to a number of embodiments of the present disclosure. The appliance 100, illustrated in the embodiment of FIG. 1A, can include an upper dentition appliance (e.g., an appliance placed on the upper jaw of the patient). An upper jaw can include a maxilla and can include a number of teeth of a patient's upper dentition. The lower jaw can include a mandible and can include a number of teeth of the patent's lower dentition.

Appliances can include any positioners, retainers, and/or other removable dental appliances for finishing and maintaining teeth positioning in connection with a dental treatment. These appliances may be utilized by the treatment professional in performing a treatment plan. For example, a treatment plan can include the use of a set of appliances, created according to models described herein. Appliances, in some embodiments, can include flexible dental appliances which serve, in part, as a prosthesis for esthetics and/or dental function.

An appliance can, for example, be fabricated from a polymeric shell, and/or formed from other material, having a cavity shaped to receive and apply force to reposition one or more teeth from one teeth arrangement to a successive teeth arrangement. The shell may be designed to fit over a number of, or in many instances all, teeth present in the upper and/or lower jaw. The shell can include an interior surface (e.g., adjacent to a surface of the teeth place therein) and an exterior surface. The interior surface is configured to receive and a apply forces to the teeth therein to reposition a number of teeth of the patient, for example.

In accordance with some embodiments of the present disclosure, the appliance 100 can include a removable shell 102 formed of a first material having a number of cavities formed therein. As discussed above, the number of cavities can be shaped to receive teeth of the patient.

The appliance 100 can include an arch element 104 extending from the removable shell 102 in a lingual direction and across an arch width of the removable shell 102. The arch width of the removable shell 102, as used herein, is a space between the cavities of the removable shell 102. For instance, the arch element 104 can expand across a surface of the mouth of the patient when the dental appliance 100 is placed over the teeth of the patient. The surface of the mouth can include, for instance, a palate and/or floor of the mouth.

The arch element, as illustrated by FIG. 1A, can be formed of the first material and a structural reinforcement feature thereon. As defined herein, a structural reinforcement feature can be any structure that increases the rigidity of a portion of the appliance or increases one or more force vectors (force provided in X, Y, and/or Z axial directions). In one example, with respect to the embodiment of FIG. 1A, the arch element 104 includes areas that are corrugated 106.

As discussed above, the arch element can be designed to expand an arch of teeth of the patient. For instance, the width of the arch element can be wider than the actual arch width of the teeth of the patient in order to define the desired arch width incremental target for the teeth. An arch width of the teeth of the patient can include a distance between teeth of the left posterior side of the patient's dentition and teeth of the right posterior side of the patient's dentition. As an example, the arch element can be 0.25 millimeters wider than the arch width of the teeth of the patient.

The element 104 as shown is designed to provide structural reinforcement to the posterior section but also allows flexibility in the anterior section, for example, if anterior transverse force is not desired. An advantage of this flexibility would be to ease the insertion force.

In some embodiments, the arch element, or a portion thereof, can be made from a second material that can be different in at least one material property (e.g., chemical property of a material, weight of material used, mixture of chemicals used, etc.) than the first material. For instance, the rigidity of the second material can apply a force to at least a portion of the number of teeth in a transverse direction (e.g., horizontal direction) to expand the arch of teeth of the patient.

Figure 5:
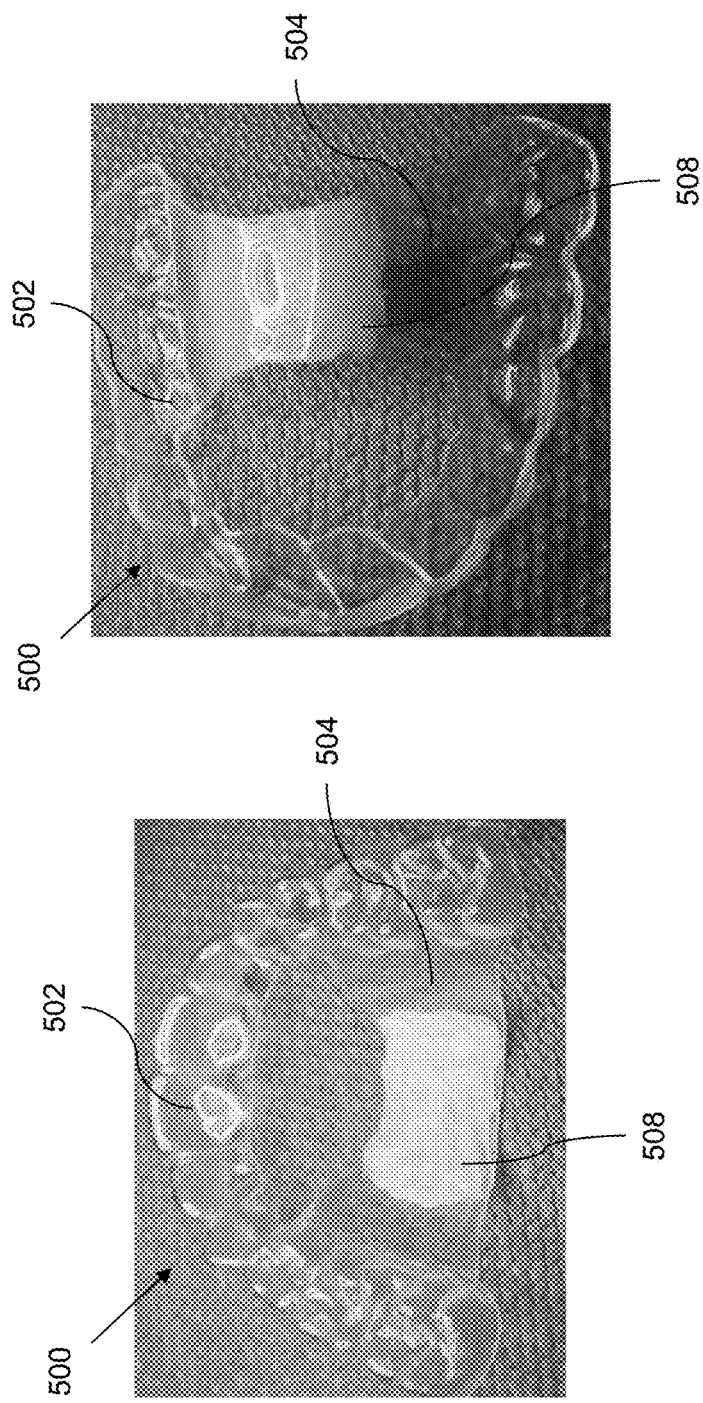
FIG. 5 illustrates an example of an appliance having a structural reinforcement material according to one or more embodiments of the present disclosure.

In some embodiments, the first material of the arch element can form a first layer and the second material of the arch element can form a second layer (e.g., as illustrated in the embodiment of FIG. 5). The first layer of the first material can be formed integrally with and of a same material as the removable shell 102, for instance. The second layer of the second material can be formed in a separate process and attached to the first layer of the first material, for example (e.g., as discussed further herein).

In some embodiments, the arch element can follow contours of a surface of the mouth of the patient when the appliance 100 is placed over the teeth of the patient. For example, the arch element can be shaped to substantially follow the contours of the palate of the patient. This can be accomplished, for example, by taking a mold or scan of the surface of the palate of the patient and then forming the surface of arch element to substantially match the mold/scan surface (i.e., the surface may not be identical, as the arch element may be designed to be wider as discussed above and therefore is not an identical copy of the mold/scan surface, and therefore may substantially match, but not be identical).

The contours of the palate in the appliance may be interpolated in anticipation of a stretching of the tissues during the expansion, in order to better accommodate the seating of the appliance in the patient's mouth. In other words, the shape of the appliance is designed to include an expected stretching of the patient's palatal or lower lingual tissues during dental expansion, and not just a movement of the teeth.

In some embodiments, one side of the arch element 104, can be adjacent to and/or in contact with a tongue of the patient. The other side of the arch element can, for example, be adjacent to and/or in contact with a surface of the patient's mouth (e.g., the palate and/or floor of the patient's mouth). Further, as discussed herein, in some embodiments, using the patient's mouth mold and/or scan data, the transpalatal arch may be designed to contact the palate (e.g., if more support is desired) or it may be designed not to have contact (e.g., for patient comfort).

The appliance 100 can be used for repositioning the number of teeth of the patient concurrently with expansion of the arch of teeth of the patient utilizing the arch element. The expansion of the arch of teeth can include movement of posterior teeth (e.g., molars) and/or other teeth of the arch of the patient in a transverse direction and/or stretching of the maxillary suture of the patient (e.g., separates the maxillary halves in the region of the suture), along with a stretching of the surrounding soft tissues (e.g., the palatal gingiva) during the expansion.

The simultaneous treatment of misalignment of a patient's dental arch (e.g., insufficient dental arch width) in conjunction with teeth alignment issues (e.g., rotation, tipping, etc.) can, for example, potentially eliminate a second phase of a two phase treatment protocol, make the second phase less complex or a little more comfortable for the patient, shorten treatment times when compared to current linear two-phase treatment protocols that first treat the misalignment of a patient's dental arch followed by treatment of misalignment of the patient's teeth. That is, the arch element can, in accordance with a number of embodiments, avoid and/or not interfere with engagement of the removable shell 102 with the teeth therein and thereby allow for correction of various tooth misalignment issues during the arch expansion process so that both arch expansion and alignment correction occurs in tandem rather than as separate phases.

Although the present embodiment of FIG. 1A illustrates an appliance for an upper dentition of a patient, embodiments are not so limited. Appliances, in accordance with some embodiments, can include an appliance for a lower dentition of a patient and/or an appliance for an upper dentition and a lower dentition.

In some such embodiments, the arch element extending from a surface of an appliance for a lower dentition can substantially follow the contours of a portion of the floor of the patient's mouth. While the lower arch (i.e., mandible) does not contain a suture that can be split as the upper arch does, the same principles of appliance design described herein may be applied even in the lower in order impart greater transverse stability and/or force through the lower arch appliance to more effectively deliver transverse forces to the lower dentition for dental expansion purposes.

In some such embodiments, since a generally horizontal span across the bottom of the patient's mouth may not be suitable for positioning of an arch element (e.g., because the tongue is in the way), an appliance of the present disclosure may include reinforced portions of the dental appliance that impart forces to help dentally expand the lower arch of the patient. For example, a portion of the arch element may be positioned in front of the tongue of the patient or in close proximity to the tongue in order to impart a horizontal force and the shell may be designed to transfer or redirect the resulting anterior force generated by the tongue towards the back portion of the jaw of the patient (e.g., closer to the molars).

In some embodiments, a first appliance can be placed over the upper dentition and a second appliance can be placed over the lower dentition of the patient. The first appliance and the second appliance can each have an arch element.

The arch element of the first appliance and the arch element of the second appliance can expand the dental arch of the upper dentition and the dental arch of the lower dentition, respectively, to the same degree. Or in the case of Class II or Class III correction where a disproportionate amount of expansion/constriction is needed, the amounts can be coordinated so that the expansion targeted is suitable for the desired amount of anterior-posterior bite change.

In some embodiments of the present disclosure, the appliance 100 can be a portion of a treatment plan. For instance, the treatment plan can include a series of appliances designed to incrementally implement a treatment plan. Each of the series of appliances can be a stage of the incremental treatment plan, for instance. The series can be used for treating misalignment of teeth of a patient and/or misalignment of one or more arches of teeth of the patient. In some such embodiments, one arch can be expanded while the other arch is not expanded or both arches can be expanded simultaneously. Or one arch can be expanded while the other one is constricted.

For instance, a first appliance, of a series of appliances designed to incrementally implement a treatment plan can comprise a first shell formed of a first material having a plurality of cavities therein designed to receive teeth of a first jaw. The first appliance can include a first arch element formed of a first layer of the first material and a second layer of the second material different than the first material.

The first arch element can extend from the first shell across an arch width of the first shell. For instance, the first arch element can have a first width specific to a first stage of the treatment plan and/or can be designed to expand an arch of the teeth of the patient.

A second appliance, of the series of appliances, can comprise a second shell having a plurality of cavities therein designed to receive teeth of the first jaw. The second appliance can include a second arch element. For example, the second arch element can have a second width specific to a second stage of the treatment plan.

The second width can be wider than the first width. For instance, the second width can include an incremental increase in width as compared to the first width. The successive incremental increase in the arch width of the appliances corresponds to the desired gradual increase in the actual physical arch of the patient.

In accordance with some embodiments of the present disclosure, the series of appliances can include a third appliance. The third appliance can include a third shell having a plurality of cavities therein designed to receive teeth of the second jaw (e.g., the lower jaw). For instance, the third appliance can include a third arch element designed to expand the arch of teeth of the patient. The third arch element can have a third width specific to the first stage of the treatment plan.

In such an embodiment, the first appliance and third appliance can be for a first stage of the treatment plan. For instance, a patient can place the first appliance over the teeth of the first jaw (e.g., upper jaw) and can place the third appliance over the teeth of the second jaw (e.g., lower jaw). The first arch element of the first appliance and the third arch element of the third appliance can be designed to expand the arch of teeth of the first jaw and the arch of teeth of the second jaw to a same degree (e.g., equal distance) based on the first width and the second width. Equal distance in expansion amount is desirable if the upper and lower arches are already in good coordination and no front-to-back change in the bite is desired or planned.

In various embodiments, the series of appliances can include a fourth appliance. The fourth appliance can include a fourth shell having a plurality of cavities therein designed to receive teeth of the first jaw. The fourth appliance may not include an arch element and/or can include a fourth arch element, for example.

Although the present embodiments illustrate two stages of a treatment plan, embodiments in accordance with the present disclosure are not so limited. Treatment plans can include a variety of number of stages, including more or less than two treatment stages. At least a portion of the stages can include treatment for gradual expansion of an arch of teeth of a patient. Alternatively and/or in addition, one or more of the stages may not include arch elements, in various embodiments.

In an example embodiment, a system can include: a first appliance, of a series of appliances designed to incrementally implement a treatment plan, having an arch element shaped to span at least a portion of the surface of a patient's palate, wherein the arch element is designed to expand an arch of the teeth of the patient, wherein the arch element has a width specific to a first stage of the treatment plan and one or more tooth engagement structures and wherein each structure contacts at least one of a surface of a tooth or a surface of the patient's gingiva and imparts a force thereto. A second appliance, of the series of appliances, can include: a second arch element shaped to span at least a portion of the surface of a patient's palate, wherein the second arch element is designed to expand the arch of the teeth of the patient, wherein the arch element has a width specific to a second stage of the treatment plan and one or more tooth engagement structures and wherein each structure contacts at least one of a surface of a tooth or a surface of the patient's gingiva and imparts a force thereto.

Figure 1B:
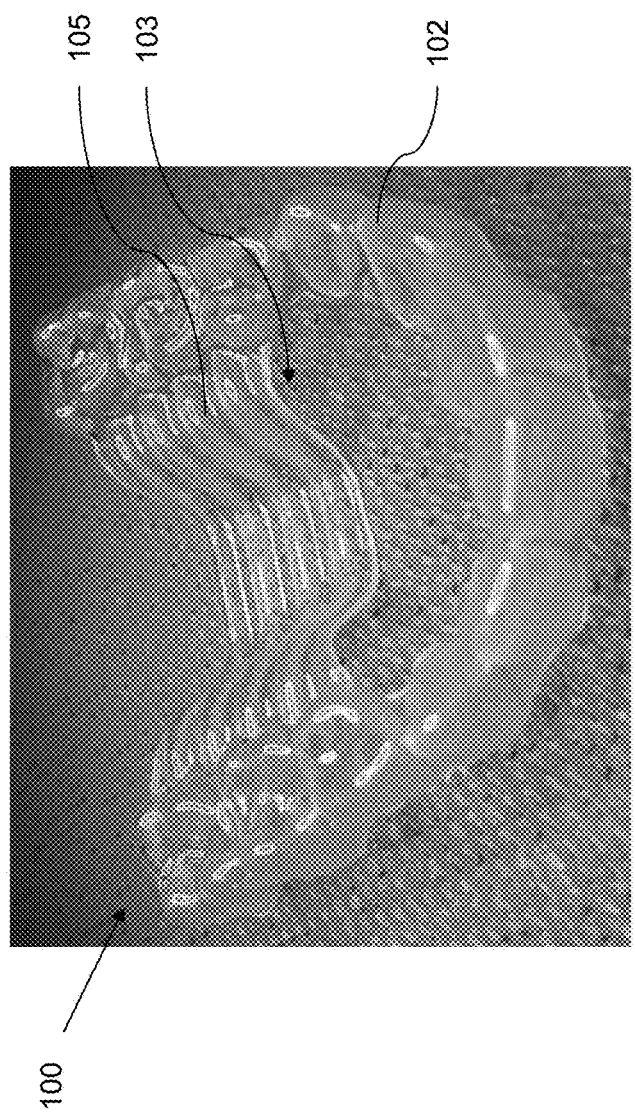
FIG. 1B illustrates another example of an appliance having a structural reinforcement feature provided thereon according to a number of embodiments of the present disclosure.

FIG. 1B illustrates an example of an appliance according to a number of embodiments of the present disclosure. Similar to the embodiment illustrated in FIG. 1A, the appliance 100, illustrated in the embodiment of FIG. 1B, can be utilized as an upper dentition appliance (e.g., an appliance placed on the upper jaw of the patient).

In accordance with some embodiments of the present disclosure, the appliance 100 can include a removable shell 102 formed of a first material having a number of cavities formed therein. As discussed above, the number of cavities can be shaped to receive teeth of the patient.

The appliance 100 can include an arch element 103 extending from the removable shell 102 in a lingual direction and across at least a portion of the arch width of the removable shell 102. The arch width of the removable shell 102, as used herein, is a space between the cavities of the removable shell 102.

For instance, the arch element 103 can span across a surface of the mouth of the patient when the dental appliance 100 is placed over the teeth of the patient. The surface of the mouth can include, for instance, a palate and/or floor of the mouth. In such an embodiment, the arch element is designed to expand an arch of the teeth of the patient, wherein the arch element has a width specific to a stage of a treatment plan. Accordingly, in some embodiments, the width of the arch element is wider than an arch width of the teeth of the patient.

The arch element, as illustrated by FIG. 1B, can be fabricated having a structural reinforcement feature thereon. In the example of FIG. 1B, a number of ridges and valleys 105 are formed on the arch element 103.

The ridge and valley structure 105 can be used to provide additional rigidity to the arch element which can allow more force to be provided. In this manner, the dental appliance can be utilized to perform more applications, such as to move palatal plates, move teeth outward, and/or maintain the teeth and/or jaw in a particular orientation while musculature and bone are adjusting to the orientation and to prevent movement of the teeth or jaw back toward their initial orientation.

Although two examples of structural reinforcement features are illustrated in FIGS. 1A and 1B, any suitable structural reinforcement feature can be utilized that will increase the rigidity of the arch element.

Figure 2:
FIG. 2 illustrates an example of an appliance embodiment according to the present disclosure.

FIG. 2 illustrates an example of an appliance embodiment according to the present disclosure. In the embodiment of FIG. 2, the shell 202 of the appliance 200 has cavities to accept less than all of the teeth of the patient's jaw. For instance, in FIG. 2, the appliance has cavities for the molars of the patient. This can be beneficial as it will only apply force to those teeth, thereby focusing the forces imparted by the appliance to those teeth that are in need of adjustment at this stage in the patient's treatment. In the embodiment of FIG. 2, the appliance has an arch element 204 with a smooth surface. Embodiments of the present disclosure can be created in a variety of ways.

For example, in some embodiments, an arch element can be formed of a material using a virtual model of a palate of a patient and a virtual model of a number of teeth of the patient. The arch element can be wider than an arch width of the number of teeth of the first jaw of the patient, specific to a stage of a treatment plan, and can be shaped to substantially follow contours of the palate of the patient (that may also include modeling of anticipated changes to the palatal contours due to tissue stretching), for instance.

The palatal contours in the model can also be specifically raised in a vertical direction so that any appliance which is formed over the model is slightly raised in comparison to the actual contours of the palate. In other words, a slight gap between the actual palate and the palatal coverage portion of the appliance can be designed to be present. This gap allows the transverse benefits of the appliance design to be in effect while not necessarily requiring an exact fit of the appliance to the contours of the tissue.

A slight offset in the vertical dimension can minimize any disruption in speech, swallowing, or feel due to changes in tongue position that may result in the alteration. More importantly, intentionally raising the vertical dimension of only the palatal tissue regions has the benefit of not needing perfect modeling of any non-linear stretching that might take place in the tissue. This can greatly reduce the risk of uncomfortable pressure spots and sores caused by the appliance. Having to relieve pressure spots in the appliance can be very time consuming for the doctor, and if the appliance is thin to begin with, such adjustments can lead to weakened areas in the appliance.

A virtual model of a number of teeth of the patient can, for example, include an initial virtual dental model and/or an intermediate virtual dental model. A virtual model of the palate (and/or other tissue surfaces of the patient's mouth) can include the contours of the palate. In some embodiments, the virtual model of the palate and the virtual model of the number of teeth can include a single virtual model and/or two separate virtual models.

The arch element can be formed by a rapid prototyping process, such as, for example, by a Computer-aided manufacturing (CAM) milling, stereolithography, 3D printing, fused deposition modeling (FDM), selective laser sintering (SLS), and/or photolithography. Advantages of such techniques can include, for example, that multiple materials can be used in a single build, various cross sectional thickness's can be designed and built for rigidity, and easy fabrication of a complex organic geometry.

The arch element can be shaped to fit between the arch of the first jaw of the patient while being sized to be wider than the arch width of the number of teeth of the first jaw of the patient.

In some embodiments, the flexibility of the appliance is such that it can be compressed in the transverse direction during seating in order to activate the expansion force. This force then gets released and directed towards the teeth, soft tissues, and/or jaw bone when then the appliance is seated in the mouth.

As discussed above, in some embodiments, the arch element can be shaped to substantially follow contours of the palate of the patient using the virtual model of the palate. Alternatively and/or in addition, the arch element can be shaped to substantially follow contours of the floor of the mouth of the patient using a virtual model of the floor of the mouth.

To form an appliance, a removable shell can, for example, be formed over a set of molded teeth. The removable shell can include a number of cavities formed therein, wherein the number of cavities are shaped to receive the number of teeth of the patient. In various embodiments, the removable shell can include a second portion of the arch element formed of the same material as the number of cavities. The second portion of the arch element can be formed integrally with and/or during a same process as the number of cavities, for instance.

The material forming the first portion of the arch element can be more rigid than the material forming the second portion of the arch element, for instance. In some embodiments, the second portion of the arch element can include the same width as the first portion of the arch element.

Alternatively and/or in addition, the first portion of the arch element can be designed to be adjacent to and/or in contact with a surface of the patient's mouth (e.g., the palate and/or floor of the patient's mouth) when the dental appliance is placed over the teeth of the patient. The second portion of the arch element can be designed to be adjacent to and/or in contact with a tongue of the patient when the dental appliance is placed over the teeth of the patient.

The dental appliance can be made, for example, by thermoforming a piece of plastic over a physical dental model. The physical dental model, for instance, can represent an incremental position to which a patient's teeth are to be moved. This desired position of the patient's teeth includes any underlying desired changes to the skeletal structure which holds the teeth in place.

The physical dental models can be manufactured by downloading a Computer-aided Design (CAD) virtual dental model file into a rapid prototyping process, such as, for example, a Computer-aided manufacturing (CAM) milling, stereolithography, 3D printing, fused deposition modeling (FDM), selective laser sintering (SLS), and/or photolithography. Advantages of such techniques can include, for example, that multiple materials can be used in a single build, various cross sectional thickness's can be designed and built for rigidity, and easy fabrication of a complex organic geometry. The virtual dental model can be hollowed out or "shelled" before it is sent for manufacturing to save on material cost if printed, for example.

The dental model (e.g., set of molded teeth) can be created from a virtual model of a number of teeth of a patient. A dental model can be formed in accordance with a unique treatment file that identifies a patient, a stage of a treatment plan, the virtual model of the number of teeth, and/or whether the dental model is of the upper and/or lower dental arch.

In some embodiments, a treatment file can be accessed by a rapid prototyping apparatus machine, such as a SLA or printing, to form and/or create the dental model. The result of the dental model can include a set of molded teeth (e.g., a physical set of molded teeth). The set of molded teeth can include at least a replica of a number of teeth of the patient. The dental model can be used to make a dental appliance, for example, by creating a negative impression of the dental model using polymeric sheets of material and vacuum forming heated sheets of the polymer over the dental model, as discussed above.

For instance, a dental appliance can be created by layering a thermoformable sheet of material and/or multiple sheets of one or more materials over the dental model. The materials can include at least one polymeric material, for instance.

Generally, the dental appliance can be produced and/or formed, for example, by heating the polymeric thermoformable sheet and vacuum or pressure forming the sheet over the dental model (i.e., over a number of the teeth in the mold). The shape of the sheet of material can be designed to intentionally vary in thickness in some portions of the sheet (beyond natural variations in thickness during the shaping process) as it conforms to the mold shape. A dental appliance can, for example, include a negative impression of the dental model. The appliance and/or parts thereof may be transparent, semi-transparent, or opaque in such a way as to emulate a natural tooth shade.

Figure 3:
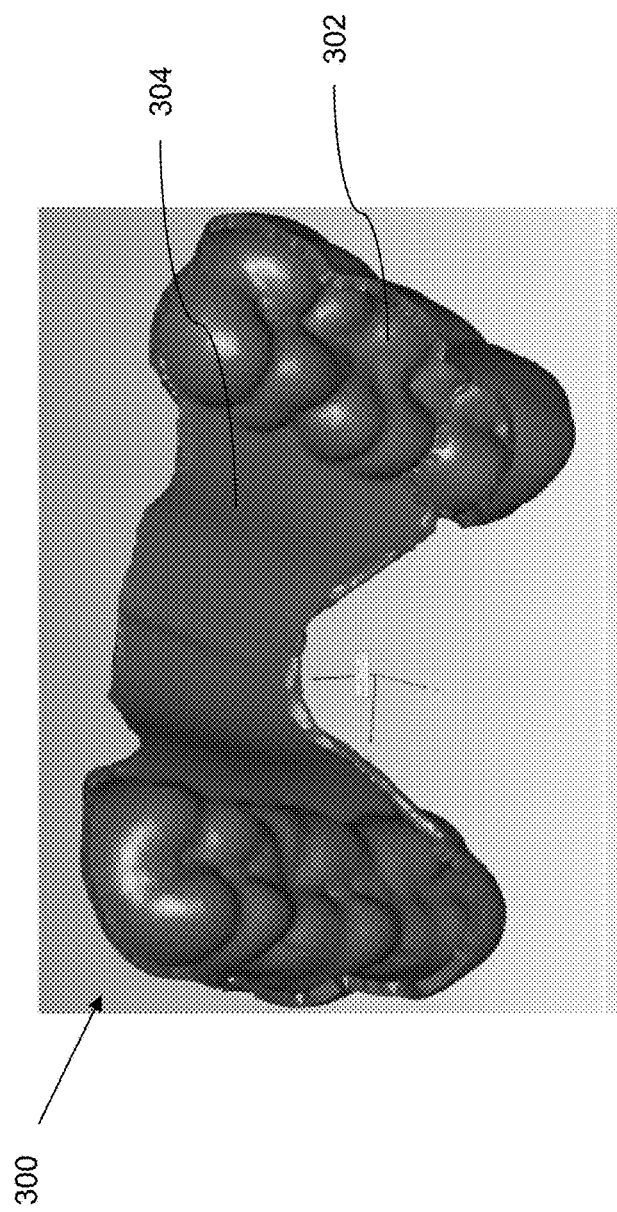
FIG. 3 illustrates virtual model of an appliance according to a number of embodiments of the present disclosure.

FIG. 3 illustrates virtual model of an appliance according to a number of embodiments of the present disclosure. As illustrated by the embodiment of FIG. 3, the virtual dental appliance 300 can include a removable shell 302, an arch element 304.

The removable shell 302 can include a number of cavities formed therein, wherein the number of cavities are shaped to receive the number of teeth of the patient. The removable shell 302, as illustrated in FIG. 3, can include a virtual removable shell, a physical removable shell, and/or material to be thermoformed over a dental model (e.g., as discussed further herein).

The model of the lower jaw, can include a virtual model of a surface of the mouth of the patient including a virtual model of the number of teeth of patient. The virtual model (e.g., the model of the lower jaw) can be used to print and/or millthe arch element.

Alternatively and/or in addition, the model of the lower jaw can include a physical set of molded teeth. A physical set of molded teeth can be created, for instance, utilizing a virtual model of the surface of the mouth and/or the teeth of the patient. The removable shell 302 can be formed over a physical set of molded teeth, in various embodiments.

Figure 4:
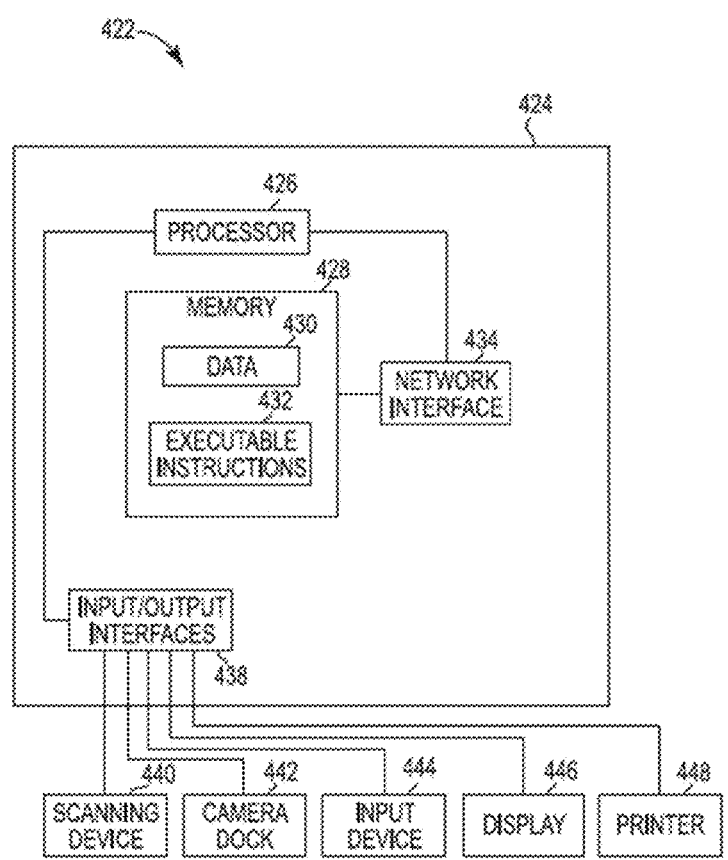
FIG. 4 illustrates an example computing device readable medium having executable instructions that can be executed by a processor to perform a method according to one or more embodiments of the present disclosure.

FIG. 4 illustrates an example computing device readable medium having executable instructions that can be executed by a processor to perform a method according to one or more embodiments of the present disclosure. For instance, a computing device 424 can have a number of components coupled thereto. The computing device 424 can include a processor 426 and a memory 428. The memory 428 can have various types of information including data 430 and executable instructions 432, as discussed herein.

The processor 426 can execute instructions 432 that are stored on an internal or external non-transitory computer device readable medium (CRM). A non-transitory CRM, as used herein, can include volatile and/or non-volatile memory. Volatile memory can include memory that depends upon power to store information, such as various types of dynamic random access memory (DRAM), among others. Non-volatile memory can include memory that does not depend upon power to store information.

Memory 428 and/or the processor 426 may be located on the computing device 424 or off the computing device 424, in some embodiments. As such, as illustrated in the embodiment of FIG. 4, the computing device 424 can include a network interface 434. Such an interface 434 can allow for processing on another networked computing device, can be used to obtain information about the patient, and/or can be used to obtain data and/or executable instructions for use with various embodiments provided herein.

As illustrated in the embodiment of FIG. 4, the computing device 424 can include one or more input and/or output interfaces 438. Such interfaces 438 can be used to connect the computing device 424 with one or more input and/or output devices 440, 442, 444, 446, 448.

For example, in the embodiment illustrated in FIG. 4, the input and/or output devices can include a scanning device 440, a camera dock 442, an input device 444 (e.g., a mouse, a keyboard, etc.), a display device 446 (e.g., a monitor), a printer 448, and/or one or more other input devices. The input/output interfaces 438 can receive executable instructions and/or data, storable in the data storage device (e.g., memory), representing a virtual dental model of a patient's dentition.

In some embodiments, the scanning device 440 can be configured to scan one or more physical dental models of a patient's dentition. In one or more embodiments, the scanning device 440 can be configured to scan the patient's dentition and/or dental appliance directly. The scanning device 440 can be configured to input data into the computing device 424.

In some embodiments, the camera dock 442 can receive an input from an imaging device (e.g., a 2D or 3D imaging device) such as a virtual camera, a printed photograph scanner, and/or other suitable imaging device. The input from the imaging device can, for example, be stored in memory 428.

The processor 426 can execute instructions to provide a visual indication of a treatment plan, a dental appliance, and/or a portion of an arch element on the display 446. The computing device 424 can be configured to allow a treatment professional or other user to input treatment goals. Input received can be sent to the processor 426 as data 430 and/or can be stored in memory 428.

Such connectivity can allow for the input and/or output of data and/or instructions among other types of information. Some embodiments may be distributed among various computing devices within one or more networks, and such systems as illustrated in FIG. 4 can be beneficial in allowing for the capture, calculation, and/or analysis of information discussed herein.

The processor 426, in association with the data storage device (e.g., memory 428), can be associated with the data 430. The processor 426, in association with the memory 428, can store and/or utilize data 430 and/or execute instructions 432 for designing a virtual appliance for a specific stage of a treatment plan and/or a series of virtual appliances for a treatment plan. Such data can include the virtual dental model and/or virtual model of a surface of a patient's mouth (e.g., palate and/or floor of the mouth).

The processor 426 coupled to the memory 428 can cause the computing device 424 to perform a method including, for example, providing a virtual model of a dental appliance having a shell configured to reposition a number of teeth of a patient. The virtual model of the dental appliance can include a second portion of an arch element. In various embodiments of the present disclosure, the processor 426 coupled to the memory 428 can cause the computing device 424 to perform the method including providing a virtual model of a first portion of an arch element (e.g., as illustrated in FIG. 3).

The virtual model of the dental appliance can, in some embodiments, be used to create a physical dental appliance. For example, dental appliance structural data can be stored in memory and used by an appliance manufacturing device to fabricate an appliance based upon the dental structural data. For instance, the memory can contain executable instructions to operate a thermoforming or direct fabrication device to form a dental appliance using those techniques.

As discussed above, in some embodiments, the arch element, or a portion thereof, can be made from a second material that can be more rigid than the first material. For instance, the rigidity of the second material can apply a force to at least a portion of the number of teeth in a transverse direction (e.g., horizontal direction) to expand the arch of teeth of the patient. In some embodiments, the rigidity of the second material can generate a necessary palatal expansion force to un-fuse the suture of the maxilla and/or move the portions of the maxilla with respect to each other, among other uses as discussed herein.

In some embodiments, the first material of the arch element can form a first layer and the second material of the arch element can form a second layer (e.g., as illustrated in the embodiment of FIG. 5). The first layer of the first material can be formed integrally with and of a same material as the removable shell 102, for instance.

The second layer of the second material can be fabricated in a separate process and attached to the first layer of the first material, for example (e.g., as discussed further herein). In some embodiments, the second layer may be the same thickness or a thicker layer of the material of the first layer.

In such embodiments, these two layers can be referred to as a first portion and a second portion of the arch element.

The first portion and the second portion of the arch element can be wider than the arch width of the number of teeth of the first jaw of the patient. For instance, the arch element can be shaped to substantially follow contours of the palate of the patient and/or the floor of the mouth of the patient, in some embodiments. The palatal contour in the model can be raised in order to result in a uniform relief gap between the appliance and the actual contour of the palate. The physical first portion can be formed of a material that is more rigid than the material forming the second portion.

In some embodiments, in order to direct force from the arch element to other portions of the shell, a more rigid material may be applied between the arch element and other portions of the shell (e.g., a rigid material is applied over and/or under the shell material or encapsulated within layers of shell material). Additionally, the rigid material used to form the arch element and/or force directing portions can be reinforced by a reinforcement material (e.g., a metallic sheet or wire material provided to the second material).

In one example method embodiment, the method of forming a dental appliance, includes: forming a first virtual arch element using physical data of a palate and a number of teeth of a patient, wherein the arch element is wider than an arch width of the number of teeth of a first jaw of the patient, specific to a stage of a treatment plan and forming one or more virtual tooth engagement structures connected to the arch element and wherein each structure contacts a surface of a virtual tooth and imparts a virtual force thereto. Such embodiments can further include forming a second virtual arch element using physical data of a palate and a number of teeth of a patient, wherein the second arch element corresponds impart a force on one or more teeth according to a second stage of the treatment plan and replacing the first virtual arch element with the second virtual arch element.

The second virtual arch element can be formed, for example, by using physical data of a palate and a number of teeth of a patient, wherein the second arch element corresponds impart a force on one or more teeth according to a second stage of the treatment plan. Second one or more virtual tooth engagement structures connected to the second virtual arch element using physical data of a palate and a number of teeth of a patient can be formed, wherein the second one or more tooth engagement structures correspond to move one or more teeth according to a second stage of the treatment plan.

In some embodiments, prior to forming the second one or more virtual tooth engagement structures that correspond to move one or more teeth according to a second stage of the treatment plan, the location of the teeth is calculated based upon a movement of an arch of the patient accomplished by one or more estimated forces applied by the first arch element and first one or more virtual tooth engagement structures. This can be beneficial in better matching the virtual adjustment of the patient's mouth to what will actually occur in the patient's mouth, among other benefits.

In some embodiments, the method can further include defining a space between two virtual teeth or a virtual tooth and another feature of a patient's mouth based upon a calculated movement of an arch of the patient accomplished by one or more estimated forces applied by the first arch element and first one or more virtual tooth engagement structures and designing the second virtual tooth engagement structures to maintain the defined space. This can be beneficial wherein a space will be needed at a later time in treatment and/or as teeth are erupting, among other benefits.

As noted herein in some embodiments, the virtual appliance or data therefrom can be used to fabricate a physical appliance to be used in a patient's mouth. For example, in some embodiments, a method can further include forming a physical arch element based on the virtual arch element and one or more physical tooth engagement structures connected to the arch element and wherein each structure contacts a surface of a virtual tooth of a patient and imparts a virtual force thereto.

It should be noted that when first and second are used to describe items in this disclosure, it is only meant that one item comes before the next and does not indicate that the items be the first and second items in a series of multiple items. For example, a first item may be the third item in a series of items and the second item may be the sixth item in a series and the terms first and second are used to indicate that the first comes before the second in the series even though there may be more items in the series.

FIG. 5 illustrates an example of an appliance having a structural reinforcement material according to one or more embodiments of the present disclosure. In the embodiment of FIG. 5, the appliance 500 is shown at two different perspectives. The arch element 504 includes multiple materials (e.g., a first material layer which, in this case, is the same type of material as the shell 502, and a second material layer 508, which is a different material).

The first portion of the arch element can be connected to the second portion of the arch element to form the dental appliance. The arch element can, for example, be designed to provide a force to at least a portion of the number of teeth in a transverse direction to expand the arch of the teeth of the first jaw of the patient.

The first portion of the arch element and the second portion of the arch element can be connected in a variety of ways, in accordance with some embodiments of the present disclosure. For instance, the first portion of the arch element can be connected to the second portion of the arch element by thermoforming the removable shell over the set of molded teeth with the first portion of the arch element placed within the set of molded teeth (i.e., encapsulated by).

In some embodiments, an agent (e.g., a binding material) can be added to connect the first portion of the arch element to the second portion of the arch element created by thermoforming the removable shell. The first and second portions may also be secured to each other through ultrasonic welding or other techniques that allow adhesion without the need for an intermediary substrate such as a solvent or adhesive.

In accordance with some embodiments of the present disclosure, the first portion of the arch element can be connected to the second portion of the arch element by adhering the first portion and the second portion subsequent to forming the first portion of the arch element and the removable shell. In some embodiments, an agent can be utilized to cause the first portion of the arch element to adhere to the second portion of the arch element, however, in some embodiments, multiple materials used to form the first portion and second portion may be bonded without the use of an agent (e.g. ultrasonic welding, laser spot welding). The first portion can also be cured into place in direct contact with the dental model (e.g. a liquid resin such as polyacrylic painted onto the model and subsequently hardened through chemical or light cure) and then joined to the second material which is thermoformed over the first material to create an adherent bond between the two materials.

In various embodiments, the first portion can include a number of features (e.g., as discussed further herein). Connecting the first portion to the second portion of the arch element can include thermoforming the removable shell over the set of molded teeth with the first portion of the arch element placed within the set of molded teeth. The thermoformed material (i.e., the material the removable shell is formed of) can surround the number of features of the first portion of the arch element to connect the first portion to the second portion of the arch element.

The removable shell 502 can include the number of cavities and a second portion of the arch element 506. The second portion of the arch element 506 can be formed concurrently with and/or of the same material as the cavities, for instance, using the model of the lower jaw. The material forming the first portion of the arch element 504 can be more rigid than the material forming the second portion of the arch element 506.

The first portion of the arch element 504 can be connected to the second portion of the arch element 506 to form a dental appliance. For example, the first portion of the arch element 504 can be placed within the physical set of molded teeth (e.g., the model of the lower jaw). An agent can be added to the second portion of the arch element. The first portion of the arch element 504 and the second portion of the arch element 506 can be connected as the removable shell 502 is thermoformed over the set of molded teeth. That is, the first portion of the block element 504 can be encapsulated in the set of molded teeth and can be adhered to the second portion of the arch element 506 utilizing an agent.

Alternatively, the first portion of the arch element 504 can be connected to the second portion of the arch element 506 subsequent to forming the first portion of the arch element 504 and the removable shell 502. For instance, the removable shell 502 can be thermoformed over the physical set of molded teeth. Subsequently, the first portion of the arch element 504 can be adhered to the second portion of the arch element 506. The portions of the arch element 504, 506 can be adhered using an agent or through means not requiring an agent (such as ultrasonic welding), for instance.

Some embodiments of the present disclosure can be provided in multiple parts. This can be beneficial, for example, where the palate has been expanded, but the movement of teeth, by the cavities and other appliance structures is still ongoing. In such cases, an appliance such as that shown in FIG. 6A or 6B, may be suitable.

Figure 6A:
FIG. 6A illustrates an example of an appliance having a removable arch element according to a number of embodiments of the present disclosure.
Figure 6B:
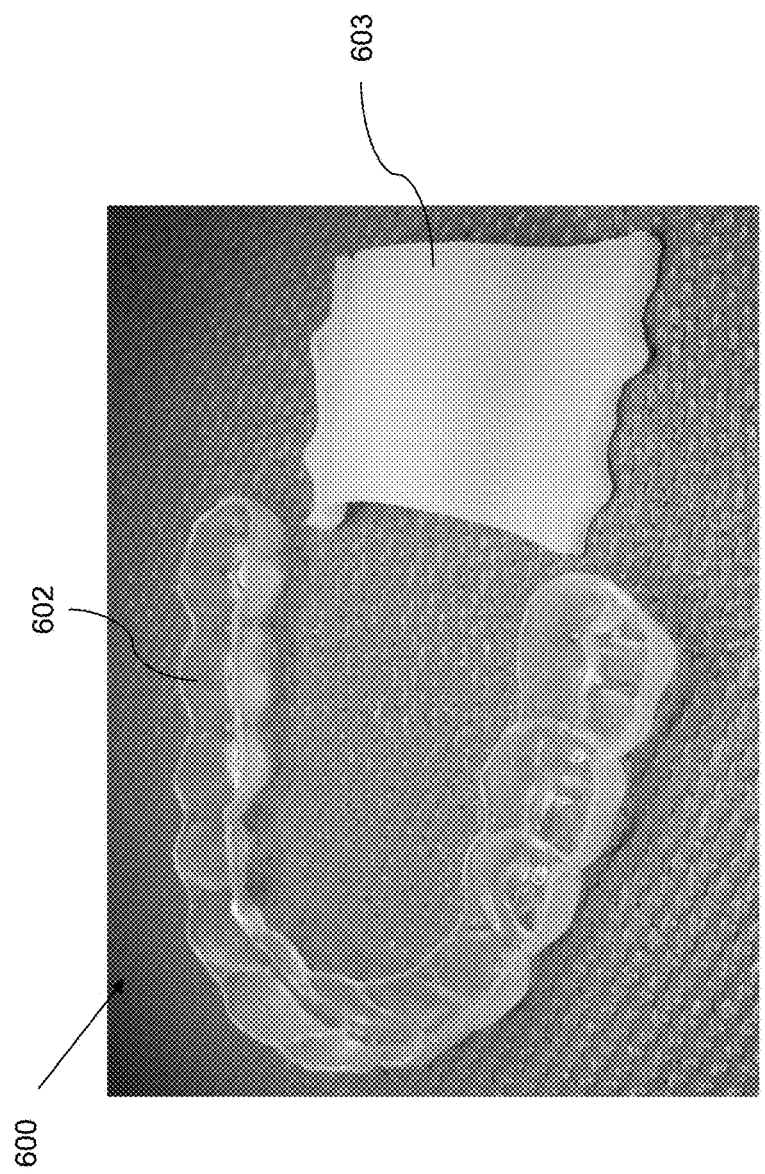
FIG. 6B illustrates an example of an appliance having a removable arch element according to a number of embodiments of the present disclosure.

FIGS. 6A and 6B illustrate an example of an appliance having a removable arch element according to a number of embodiments of the present disclosure. In the embodiments of FIGS. 6A and 6B, the appliance 600 has a shell 602 with a mounting element 610 (as shown in FIG. 6A) thereon to engage the arch element 604.

The mounting element and arch element can be affixed together by any suitable mechanism and can be either releasably or permanently affixed together. Some examples of affixation mechanisms include, sliding a flange into a slot, placing a tab into an aperture, chemical bonding, adhesive bonding, among many other affixation mechanisms. In the embodiment of FIG. 6A, the edges of the arch element that will be adjacent to the shell can be slid into a notch or channel formed in the shell (the embodiment of FIG. 6A has a raised channel formed therein). This engagement can be mechanically fixed (by a locking mechanism or frictional engagement or by bonding the two parts together chemically or with an adhesive.

In the embodiment of FIG. 6B, an arch element 603 is attached to a shell 602 to form an appliance 600. In this embodiment, the arch element 603 is formed from a material different than that of shell 602.

Materials having different characteristics can be added or in some embodiments, one arch element can be interchanged with another. For example, if it is desired that the arch element be more rigid than the shell, then a more rigid material may be used (as in this embodiment) or added as a layer (to an arch element of one or more other materials, such as that of FIG. 6A or FIG. 9) to add rigidity to the arch element. In another embodiment, the arch portion of the appliance may already have rigidity, but may lose its rigidity over time, so an arch element of a different material can be added to provide resiliency which may extend the period in which the original arch material may be usable for its purpose.

In various embodiments, a first arch element can be used and then a second arch element having a different characteristic may be affixed in place of the first arch element. For example, an arch element having a first force providing physical characteristic may be utilized and then that arch element may be removed from the appliance and replaced by an arch element having a second force providing characteristic. This can be beneficial in embodiments where the shell can be reused from one phase of treatment to another and as such, the arch element can be replaced rather than an entirely new appliance having to be fabricated and used. The different characteristic can be different from one or both of the shell and/or the first arch element. Examples of different physical characteristics include: rigidity, resiliency, color, and thickness profile (thickness at any point along the second arch element maybe different than the thickness at a corresponding point on the first arch element).

In some embodiments, the arch element can be removed and the appliance can continue to be worn in the patient's mouth without the arch element. In such embodiments, the appliance can, for example, continue to maintain the position of one or more teeth and/or can continue to adjust the positon and/or orientation of one or more teeth.

FIG. 7 illustrates an example of an appliance having an anterior tab arch element according to a number of embodiments of the present disclosure. FIG. 7 provides an appliance 700 having a shell 702 with a tab 705 thereon to provide additional rigidity and/or palate expansion force. The anterior tab 705 is a small tab on lingual side of arch. It may be used to increase structural integrity of the appliance in the transverse direction between the two ends of the jaw. In some embodiments, lingual tab feature may run along one or more portions of or the entire span of arch. The cross sectional geometry of the lingual tab can be varied uniformly or non-uniformly along its length to provide additional rigidity and/or force to adjust the palate.

Figure 8:
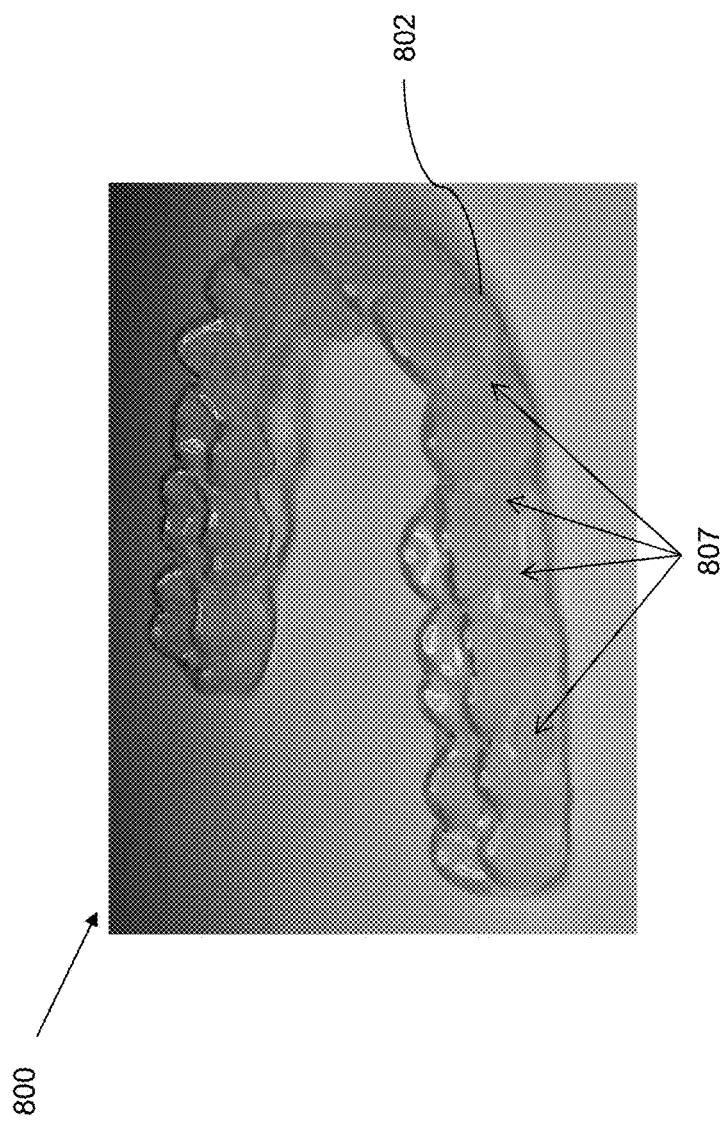
FIG. 8 illustrates an example of an appliance having a rib feature according to a number of embodiments of the present disclosure.

FIG. 8 illustrates an example of an appliance having a rib feature according to a number of embodiments of the present disclosure. FIG. 8 provides an appliance 800 that has one or more rib features 807 on the surface of the shell 802. These features are areas that are thicker than other portions of the appliance body thickness and therefore provide addition rigidity and/or force.

Additionally, the ribs are elongate shapes that can be oriented in different directions along the surface of the shell 802. This enables them to provide forces in specialized directions to precision the forces provided to the teeth from the appliance. In the illustrated embodiment, of FIG. 8, the ribs have been thermoformed in a particular geometry (planned through the aid of the executable instructions in the computing device) to provide added rigidity to the posterior section of the dental appliance.

For example, in some embodiments, a rib feature can be positioned in the buccal and/or lingual sections between the cavities for the crowns to strengthen the appliance in the transverse direction, so individual teeth can be moved as a segment. In a mixed dentition case, if a primary tooth is lost during treatment, such an embodiment can help preserve the palatal expansion force, since the posterior section is being expanded as a segment.

FIG. 9 illustrates an example of an appliance having an arch element connecting the posterior sides of the arch according to a number of embodiments of the present disclosure. In the embodiment of FIG. 9, the appliance 900 includes a shell 902 with an arch element 904 spanning across the palate. In this embodiment, the arch element 904 does not cover the entire palate of the patient, but rather, spans a portion of the palate and leaving a portion uncovered. Such an embodiment may be more comfortable for the patient and may be easier to place and remove, among other benefits.

FIG. 10 illustrates an example of an appliance having a full palatal arch element according to a number of embodiments of the present disclosure. In the embodiment of FIG. 10, the appliance 1000 includes a shell 1002 with an arch element 1004 spans the entire palate surface (in the anterior-posterior direction between the left and right jaw portions of the shell 1002. In this embodiment, the arch element 1004 spans the entire palate of the patient (up to the back edge if the back molars or the molars that are second from the back). Such an embodiment may be easier to manufacture and will reduce edges that may be uncomfortable to the patient, among other benefits.

FIG. 11 illustrates an example of an appliance having an extended gingival feature thereon according to a number of embodiments of the present disclosure. The embodiment of FIG. 11 provides an appliance 1100 including a shell 1102 having an extended gingival feature 1109 to provide additional rigidity and/or palate expansion force.

The extended gingival feature 1109 is an extension of the appliance that is contoured to follow the shape of the gingiva. This type of arch element may be used to increase structural integrity of the appliance in the transverse direction between the two ends of the jaw. In some embodiments, extended gingival feature may run along one or more portions of or the entire span of arch.

Further, the cross sectional geometry of the extended gingival feature can be varied uniformly or non-uniformly along its length to provide additional rigidity and/or force to adjust the palate. For example, the extended gingival feature can be shaped to match the contour (e.g., in two or three dimensions) of the physical gingiva upon which the extended gingival feature will be placed.

The extension of the gingival cut line at the time of manufacturing may accomplish what the anterior tab feature does by using the actual gingival surface to support the transverse force to increase the rigidity of the appliance and/or provide force to adjust the palate in the transverse direction. This feature may also help with appliance retention for short crowns found in mixed dentition cases, among other benefits.

Embodiments of the present disclosure can also provide other beneficial functions. For example, embodiments can maintain space in the patient's mouth when the patient's primary and permanent dentition have a size discrepancy.

For instance, unlike the anterior teeth, the permanent premolars may be smaller than the primary teeth they replace. On average, the mandibular primary second molar is 2 mm larger than the second premolar and, in the maxillary arch, the primary second molar is only 1.5 mm larger. The primary first molar is only 0.5 mm larger than the first premolar. Accordingly, on average, this results in 2.5 mm of space, called leeway space, in the mandibular arch and 1.5 mm in the maxillary arch. The leeway space is usually taken by mesial movement of the permanent molars (the permanent first molars move mesially relatively rapidly).

This creates an opportunity to gain arch length and relieve crowding by stopping the first molar mesial movement by, for example, using a pontic along with the appliance by filling the appliance tooth space and leaving clearance for erupting tooth. The filled pontic material can be used to keep the first molar from moving into the leeway space while allowing the permanent premolar to erupt.

Figure 12A:
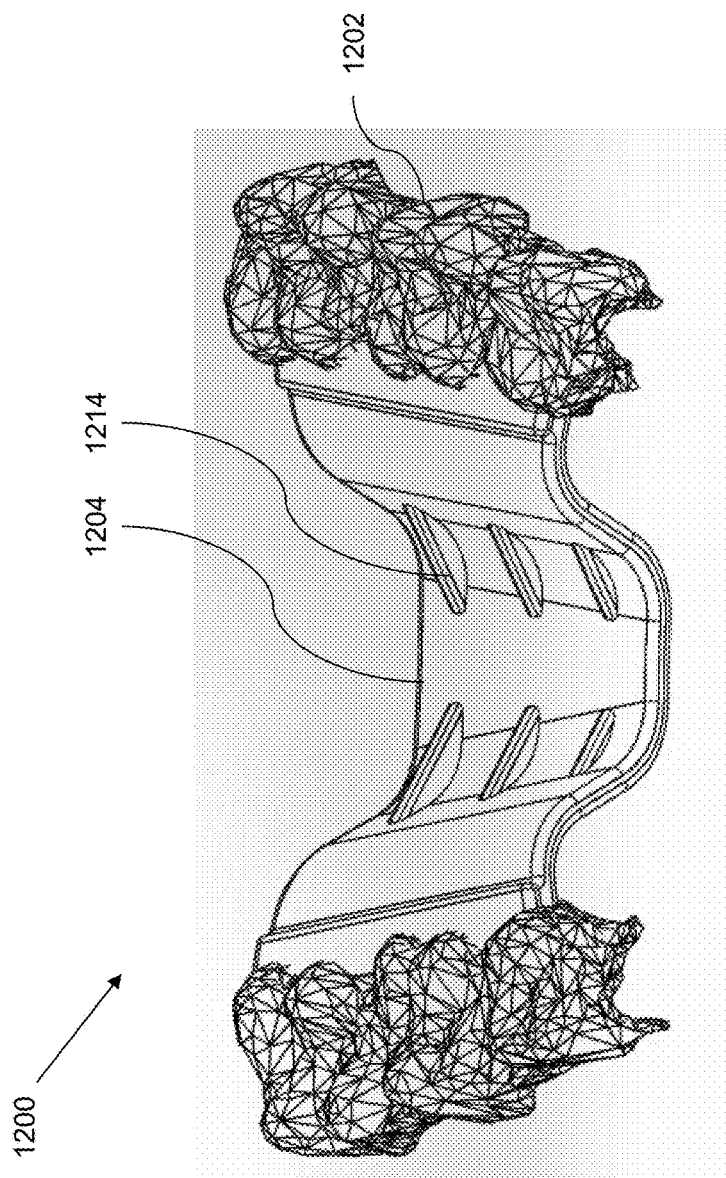
FIG. 12A illustrates an example of an appliance according to a number of embodiments of the present disclosure.
Figure 12B:
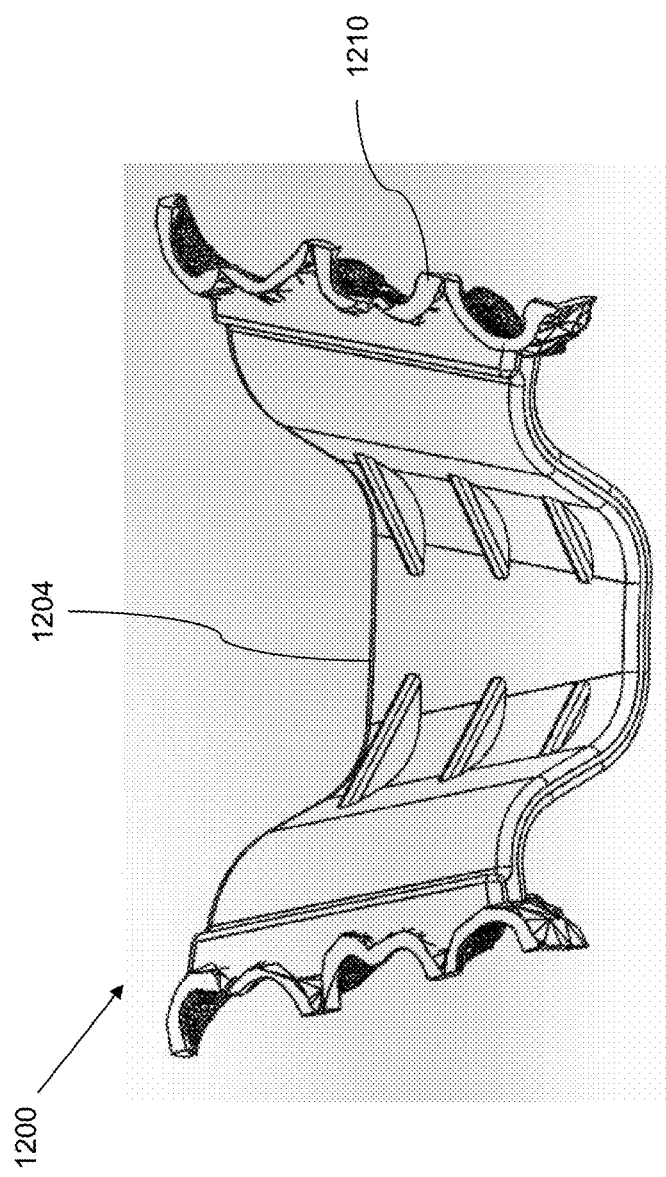
FIG. 12B illustrates an example of an appliance according to a number of embodiments of the present disclosure.
Figure 12C:
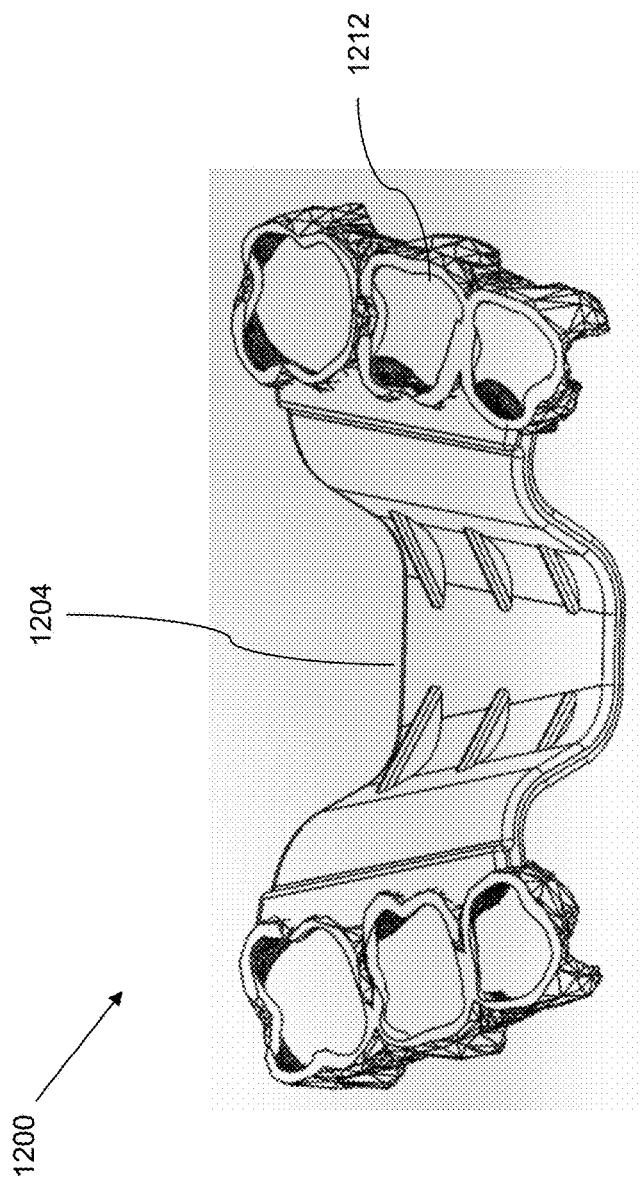
FIG. 12C illustrates an example of an appliance according to a number of embodiments of the present disclosure.

FIGS. 12A, 12B, and 12C illustrate examples of appliances according to a number of embodiments of the present disclosure. In the embodiment of FIG. 12A, an appliance 1200 has one or more tooth engagement structures, in this case, a shell 1202 with cavities, and an arch element 1204 formed thereon. Also illustrated in the embodiment of FIG. 12 A are structural reinforcement features in the form of struts 1214. These features can be positioned in various places on the arch element to increase the rigidity of the arch element.

This may be a design that can be produced directly from a virtual model, through processes as discussed above, either as a single piece or as one or more shell and arch pieces that can be affixed together. In the embodiment of FIG. 12B, the appliance 1200 does not have a shell, but rather has an arch element 1204 and one or more tooth engagement structures 1210 to contact a surface of a tooth and impart force thereto.

It should be noted that in some embodiments, portions of the appliance may not be visible to people when they see the appliance in the patient's mouth and as such the material does not have to be clear, and this therefore allows for more options with regard to the choice of material that can be utilized. With some manufacturing processes, as discussed herein, the appliance can be fabricated from multiple materials or can be manufactured in parts wherein the parts are made from different materials and are attached together to create the appliance.

The tooth engagement structure may extend along a small portion of the side surfaces of the tooth or may extend substantially around the side surfaces of the tooth, as shown in FIG. 12C. In the embodiment of FIG. 12C, the tooth engagement structures 1212 extend around the entire side surfaces of the tooth to surround the tooth.

Such embodiments may provide more secure fitment of the appliance in the mouth of the patient, may be able to impart more force, and may be able to control that application of that force in one or more directions with respect to the tooth. This may, in some instances, allow the positon or orientation of a tooth to be adjusted while the appliance is expanding the palate of the patient.

In some embodiments, the appliance can be overlayed over an existing appliance used to adjust tooth positioning and/or orientation. For example, in an embodiment such as the one illustrated in FIG. 12A, the cavities 1202 can be sized to fit over cavities of an aligner appliance used for aligning one or more teeth or a retainer appliance used to maintain the position of one or more teeth. The aligner appliance and/or the arch adjustment appliance may have features thereon to lock the two appliances together or they may be affixed together by other means (e.g., frictionally and/or via adhesives, etc.).

As discussed herein, multiple piece embodiments can be potentially beneficial, for example, because they can be designed to have a removable portion. For instance, the lingual side connection feature can be affixed (e.g., thermoformed) on the surface of the appliance. A rigid piece, spanning across the palate, can be snapped into place and removed as needed. Alternatively, in some embodiments, a wire or spring can be used instead of the rigid piece.

In embodiments where the pieces are permanently affixed, a lingual side connection feature can be affixed (e.g., thermoformed) on the surface of the appliance to position a rigid piece spanning across the palate so it can be secured to an appliance (e.g., with adhesive). Alternatively, a wire or spring can be used instead of the rigid piece, in some embodiments.

In one such embodiment, the appliance includes an arch element shaped to span at least a portion of the surface of a patient's palate, wherein the arch element is designed to expand an arch of the teeth of the patient, wherein the arch element has a width specific to a stage of a treatment plan and one or more tooth engagement structures and wherein each structure contacts at least one of a surface of a tooth or a surface of the patient's gingiva and imparts a force thereto. In some such embodiments, one or more tooth engagement structures is a removable shell having a number of cavities formed therein, wherein the number of cavities are shaped to receive teeth of a patient.

As shown in FIG. 12B, the tooth engagement structure can extend along a portion of at least one side surface of a tooth. Further, in the embodiments of FIGS. 12A and 12C, the tooth engagement structure can extend substantially around the side surfaces of the tooth (in the embodiments of FIGS. 12A and 12C it extends all the way around) to surround the tooth.

Although the discussion above is focused on arch expansion, in some instances the arch will need to be contracted and embodiments of the present disclosure can be utilized for arch contraction cases as well. For example, in a method embodiment, the method can include a method of forming a dental appliance, including forming a first virtual arch element using physical data of a palate and a number of teeth of a patient, wherein the arch element is narrower than an arch width of the number of teeth of a first jaw of the patient, specific to a stage of a treatment plan, forming one or more virtual tooth engagement structures connected to the arch element and wherein each structure contacts a surface of a virtual tooth and imparts a virtual force thereto. In various embodiments such as those illustrated in the Figures, the tooth engagement structure can be constructed and arranged to impart force to move the tooth either positionally or orientationally or both while the appliance is adjusting (i.e., expanding or contracting) the palate of the patient.

Other benefits of embodiments of the present disclosure can include, but are not limited to: arch form control wherein the appliance has structural integrity to modify or control mandible or maxilla shape. The use of an upper and lower appliance set allows for alignment of the arch shape in either or both arches. Embodiments can also provide structural integrity to enhance and control growth as a patient matures, among other benefits.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An appliance comprising:
   a removable shell formed of a first material having a number of cavities formed therein;
   wherein the number of cavities are shaped to receive teeth of a patient;
   wherein the removable shell has an arch width between a first side of the removable shell positioned on a first side of the patient's mouth and a second side of the removable shell positioned on a second side of the patient's mouth;
   a sheet of material forming an arch element extending from the removable shell in a lingual direction and across at least a portion of the arch width of the removable shell;
   wherein the arch element is designed to expand an arch of the teeth of the patient and has a width specific to a stage of a treatment plan;
   wherein the arch element is formed of the first material and a second material, and the second material is different in at least one material property than the first material and is more resilient than the first material; and
   wherein at least a part of the arch element has a corrugated surface.

2. The appliance of claim 1, wherein the appliance provides a force when placed in the patient's mouth by being formed with the width of the arch element being wider than an arch width of the teeth of the patient.

3. The appliance of claim 1, wherein the arch element is a first arch element and is releasable from the removable shell such that the removable shell can be used in the patient's mouth without the arch element.

4. The appliance of claim 3, further comprising a second arch element that can be affixed to the removable shell in place of the first arch element.

5. The appliance of claim 4, wherein the second arch element possesses a different physical characteristic than the first arch element.

6. The appliance of claim 4, wherein the second arch element possesses a different physical characteristic than the removable shell and wherein the different physical characteristic is selected from the group including: rigidity, resiliency, color, and thickness profile.

7. An appliance comprising:
   a sheet of material forming an arch element shaped to span at least a portion of a surface of a patient's palate;

wherein the arch element is designed to expand an arch of the patient's teeth and has a width specific to a stage of a treatment plan;

wherein the arch element is formed of a first material and a second material, and the second material is different in at least one material property than the first material and is more resilient than the first material;

wherein at least a part of the arch element has a corrugated surface; and one or more tooth engagement structures, wherein each tooth engagement structure contacts at least one of a surface of a tooth or a surface of the patient's gingiva and imparts a force thereto.

8. The appliance of claim 7, wherein the one or more tooth engagement structures is a removable shell having a number of cavities formed therein, wherein the number of cavities are shaped to receive teeth of the patient.

9. The appliance of claim 7, wherein the one or more tooth engagement structures extends along a portion of the at least one side surface of a tooth.

10. The appliance of claim 7, wherein the one or more tooth engagement structures extends substantially around side surfaces of the tooth to surround the tooth.

11. The appliance of claim 7, wherein the one or more tooth engagement structures is constructed and arranged to impart force to move the tooth either positionally or orientationally while the appliance is expanding the patient's palate.

12. A system, comprising:
a first appliance, of a series of appliances designed to incrementally implement a treatment plan, comprising:
a sheet of material forming a first arch element shaped to span at least a portion of a surface of a patient's palate;
wherein the first arch element is designed to expand an arch of teeth of the patient and has a width specific to a first stage of the treatment plan;
wherein the first arch element is formed of a first material and a second material, and the second material is different in at least one material property than the first material and is more resilient than the first material; and
one or more first tooth engagement structures, wherein each first tooth engagement structure contacts at least one of a first surface of a tooth or a first surface of the patient's gingiva and imparts a first force thereto; and a second appliance, of the series of appliances, comprising:
a second arch element shaped to span at least a portion of the surface of a patient's palate;
wherein the second arch element is designed to expand the arch of teeth of the patient and has a width specific to a second stage of the treatment plan;
wherein at least a part the first arch element or the second arch element has a corrugated surface; and
one or more second tooth engagement structures, wherein each of the one or more second tooth engagement structures contacts at least one of a second surface of a tooth or a second surface of the patient's gingiva and imparts a second force thereto.

13. The system of claim 12, wherein the second arch element possesses a different physical characteristic than the first arch element and wherein the different physical characteristic is selected from the group including: rigidity, resiliency, color, and thickness profile.

14. The system of claim 12, wherein the first appliance is designed to reposition a number of teeth of a first jaw of the patient concurrently as the first arch element expands the arch of teeth of the first jaw.

* * * * *